(12) United States Patent
Ries et al.

(10) Patent No.: US 7,939,658 B2
(45) Date of Patent: May 10, 2011

(54) ENANTIOMERIC PURE BETA AGONISTS, MANUFACTURING AND USE AS A MEDICAMENTS THEREOF

(75) Inventors: Uwe Ries, Biberach (DE); Peter Sieger, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/419,505

(22) Filed: Apr. 7, 2009

(65) Prior Publication Data

US 2009/0306068 A1 Dec. 10, 2009

Related U.S. Application Data

(63) Continuation of application No. 11/686,565, filed on Mar. 15, 2007, now Pat. No. 7,534,789.

(30) Foreign Application Priority Data

| Mar. 15, 2006 | (EP) | 06111191 |
| Mar. 17, 2006 | (EP) | 06111338 |
| Mar. 17, 2006 | (EP) | 06111342 |

(51) Int. Cl.
  *C07D 413/04* (2006.01)
  *A61K 31/538* (2006.01)
(52) U.S. Cl. .................... 544/105; 514/230.5
(58) Field of Classification Search .......... 544/105; 514/230.5
  See application file for complete search history.

(56) References Cited

U.S. PATENT DOCUMENTS

| 7,056,916 B2 | 6/2006 | Konetzki et al. |
| 7,160,882 B2 | 1/2007 | Bouyssou et al. |
| 7,220,742 B2 | 5/2007 | Lustenberger et al. |
| 7,375,104 B2 | 5/2008 | Bouyssou et al. |
| 7,534,789 B2 | 5/2009 | Ries et al. |

(Continued)

FOREIGN PATENT DOCUMENTS

CA 2506082 6/2004

(Continued)

OTHER PUBLICATIONS

Vippagunta et al, "Crystalline Solids" Advanced Drug Delivery Reviews, vol. 48, pp. 3-26 (2001).*

(Continued)

*Primary Examiner* — Kahsay T Habte
(74) *Attorney, Agent, or Firm* — Michael P. Morris; Edouard G. Lebel; Wendy Petka

(57) ABSTRACT

The present invention relates to enantiomerically pure compounds of formula 1

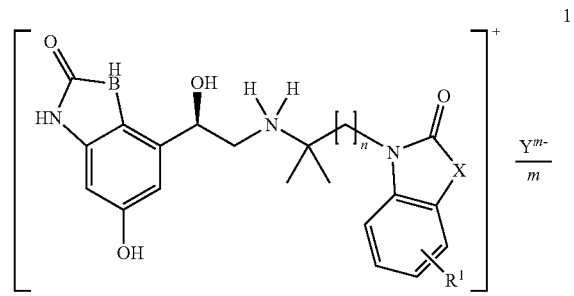

wherein the groups m, n, B, X, $R^1$, m and $Y^{m-}$ may have the meanings given in the claims and specification, methods for preparing them and their use as pharmaceutical compositions, particularly as pharmaceutical compositions for the treatment of respiratory complaints.

7 Claims, 3 Drawing Sheets

U.S. PATENT DOCUMENTS

| | | |
|---|---|---|
| 2006/0063817 A1 | 3/2006 | Bouyssou et al. |
| 2007/0027148 A1 | 2/2007 | Lustenberger et al. |
| 2008/0176744 A1 | 7/2008 | Schwogler et al. |
| 2008/0194550 A1 | 8/2008 | Bouyssou et al. |

FOREIGN PATENT DOCUMENTS

| | | |
|---|---|---|
| CA | 2552784 | 8/2005 |
| CA | 2562859 | 11/2005 |
| GB | 1571231 | 7/1980 |
| WO | 2004/045618 | 6/2004 |
| WO | 2005/070908 | 8/2005 |
| WO | 2005/111005 | 11/2005 |
| WO | 2006/032627 | 3/2006 |

OTHER PUBLICATIONS

Gavezzotti, "Are Crystal Structures Predictable?" Accounts of Chemical Research, vol. 27, pp. 309-314 (1994).*

International Search Report for PCT/EP2007/052389 mailed May 24, 2007.

* cited by examiner

ENANTIOMERIC PURE BETA AGONISTS, MANUFACTURING AND USE AS A MEDICAMENTS THEREOF

CROSS-REFERENCE TO RELATED APPLICATIONS

This application is a continuation of application Ser. No. 11/686,565 filed Mar. 15, 2007, now U.S. Pat. No. 7,534,789, which claims priority of EP06111338.7, filed Mar. 17, 2006; EP06111191.0, filed Mar. 15, 2006; and EP06111342.9, filed Mar. 17, 2006, the contents of which are incorporated herein in their entireties.

FIELD OF THE INVENTION

The present invention relates to enantiomerically pure compounds of formula 1

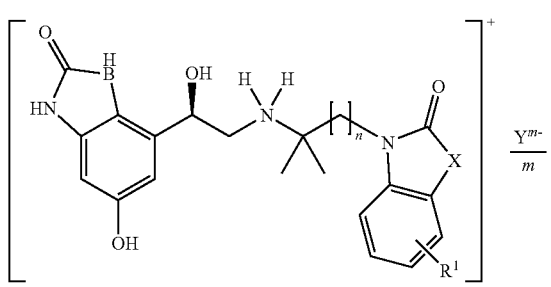

wherein the groups m, n, B, X, $R^1$, m and $Y^{m-}$ may have the meanings given in the claims and specification, methods for preparing them and their use as pharmaceutical compositions, particularly as pharmaceutical compositions for the treatment of respiratory complaints.

BACKGROUND OF THE INVENTION

Betamimetics (β-adrenergic substances) are discussed in U.S. Pat. No. 4,460,581, which proposes betamimetics for the treatment of a range of diseases.

For drug treatment of diseases it is often desirable to prepare medicaments with a longer duration of activity. As a rule, this ensures that the concentration of the active substance in the body needed to achieve the therapeutic effect is guaranteed for a longer period without the need to re-administer the drug at frequent intervals. Moreover, giving an active substance at longer time intervals contributes to the well-being of the patient to a high degree.

It is particularly desirable to prepare a pharmaceutical composition which can be used therapeutically by administration once a day (single dose). The use of a drug once a day has the advantage that the patient can become accustomed relatively quickly to regularly taking the drug at certain times of the day.

The aim of the present invention is therefore to provide betamimetics which on the one hand confer a therapeutic benefit in the treatment of respiratory complaints and are also characterized by a longer duration of activity and can thus be used to prepare pharmaceutical compositions with a longer duration of activity. A further objective of the present invention is to prepare betamimetics which, by virtue of their long-lasting effect, can be used to prepare a drug for administration once a day for treating respiratory complaints.

Another objective of the invention, apart from those mentioned above, is to prepare betamimetics which are not only exceptionally potent but are also characterized by a high degree of selectivity with respect to the $\beta_2$-adrenoceptor. In addition, the invention sets out to prepare betamimetics which because of their physicochemical properties can be used in particular for preparing pharmaceutical formulations which are particularly suitable for administration by inhalation. The invention also relates to the preparation of betamimetics, which in addition to having the above-mentioned properties, are also particularly suitable for preparing inhalable powders and suspension aerosols.

DETAILED DESCRIPTION OF THE INVENTION

Figure 1:
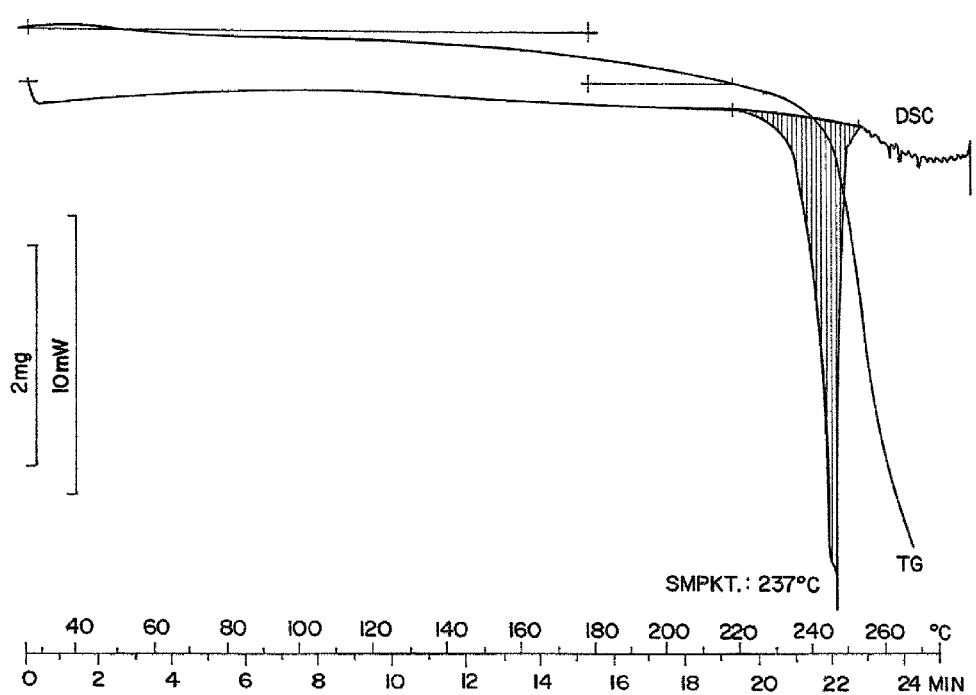
FIG. 1: Differential scanning calorimetry plot of Example 5.

The above-mentioned objectives are achieved with compounds of general formula 1. The present invention relates to enantiomerically pure compounds of formula 1:

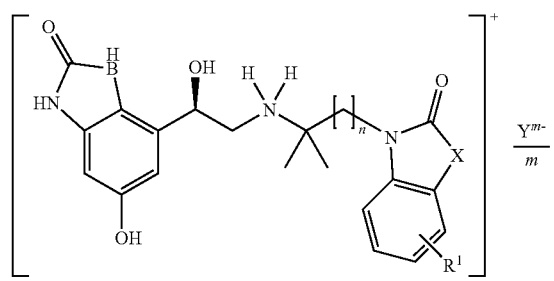

wherein
n denotes 1, 2, 3 or 4;
X denotes $CH_2$, CO, $NR^2$, S or O;
B denotes a double-bonded group of formula $CR^3R^4$—O;
$R^1$ denotes H, $C_{1-6}$-alkyl, $C_{2-6}$-alkenyl, $C_{2-6}$-alkynyl, $C_{3-6}$-cycloalkyl, $C_{1-6}$-haloalkyl, O—$C_{1-6}$-haloalkyl, halogen, OH, CN, $NO_2$, O—$C_{1-6}$-alkyl, COOH or COO—$C_{1-4}$-alkyl;
$R^2$ denotes H, $C_{1-6}$-alkyl, $C_{1-4}$-alkylene-$C_{6-10}$-aryl or $C_{1-4}$-alkylene-$C_{3-6}$-cycloalkyl, preferably H or $C_{1-6}$-alkyl;
$R^3$ denotes H or $C_{1-6}$-alkyl;
$R^4$ denotes H or $C_{1-6}$-alkyl;
$Y^{m-}$ an anion with m negative charges, preferably an anion with m negative charges selected from among chloride, bromide, iodide, sulphate, phosphate, methanesulphonate, nitrate, maleate, acetate, benzoate, citrate, salicylate, trifluoroacetate, fumarate, tartrate, oxalate, succinate, ethanedisulphonate, propanedisulphonate, benzoate and p-toluenesulphonate,
m denotes 1 or 2
optionally in the form of the tautomers, mixtures of the tautomers, hydrates or solvates thereof.

The enantiomerically pure compound shown in formula 1 corresponds to the R-enantiomer.

The compounds of formula 1 consist of a molecule with a single positive charge and an anion $Y^{m-}$ with a single charge or a corresponding l/m part of an anion $Y^{m-}$ with a single charge. Thus, for example, two molecules of formula

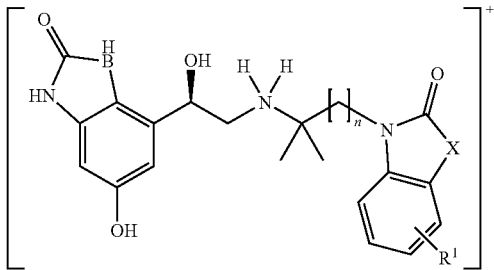

wherein the groups n, B, X and $R^1$ may have the meanings given above, may be in a crystalline formation with an anion $Y^{m-}$ having a double charge wherein m=2, such as e.g. ethanedisulphonate or propanedisulphonate.

In one embodiment the enantiomerically pure compounds of formula 1, are substituted as follows:
n denotes 1, 2 or 3; preferably 2 or 3
X denotes $CH_2$, CO, $NR^2$, S or O;
B denotes a double-bonded group of formula $CR^3R^4$—O;
$R^1$ denotes H, $C_{1-6}$-alkyl, $C_{2-6}$-alkenyl, $C_{2-6}$-alkynyl, $C_{3-6}$-cycloalkyl, $C_{1-6}$-haloalkyl, O—$C_{1-6}$-haloalkyl, halogen, OH, CN, $NO_2$, O—$C_{1-6}$-alkyl, COOH, COO—$C_{1-4}$-alkyl; preferably H, $C_{1-6}$-alkyl, $C_{1-6}$-haloalkyl, $C_{3-6}$-cycloalkyl, halogen, OH,CN, $NO_2$, O—$C_{1-6}$-alkyl, COOH or COO—$C_{1-4}$-alkyl;
$R^2$ denotes H, $C_{1-4}$-alkyl, $C_{1-2}$-alkylene-$C_{3-6}$-cycloalkyl, phenylethyl or benzyl, preferably H, $C_{1-4}$-alkyl, $C_{3-6}$-cycloalkyl-methyl, particularly preferably H, methyl or cyclopropylmethyl;
$R^3$ denotes H or $C_{1-4}$-alkyl; preferably H or methyl;
$R^4$ denotes H or $C_{1-4}$-alkyl; preferably H or methyl;
$Y^{m-}$ denotes an anion with m negative charges, preferably an anion with m negative charges selected from among chloride, bromide, iodide, sulphate, phosphate, methanesulphonate, nitrate, maleate, acetate, benzoate, citrate, salicylate, trifluoroacetate, fumarate, tartrate, oxalate, succinate, ethanedisulphonate, benzoate and p-toluenesulphonate,
m denotes 1 or 2,
optionally in the form of the tautomers, mixtures of the tautomers, hydrates or solvates thereof.

In another embodiment enantiomerically pure compounds of formula 1, are as follows:
n denotes 2 or 3
X denotes $CH_2$, CO, $NR^2$, S or O;
B denotes a double-bonded group of formula $CR^3R^4$—O;
$R^1$ denotes H, $C_{1-6}$-alkyl, $C_{1-6}$-haloalkyl, $C_{3-6}$-cycloalkyl, halogen, OH,CN, $NO_2$, O—$C_{1-6}$-alkyl, COOH or COO—$C_{1-4}$-alkyl;
$R^2$ denotes H, $C_{1-4}$-alkyl, $C_{3-6}$-cycloalkyl-methyl, particularly preferably H, methyl or cyclopropylmethyl;
$R^3$ denotes H or methyl;
$R^4$ denotes H or methyl;
$Y^{m-}$ denotes an anion with m negative charges, preferably an anion with m negative charges selected from among chloride, bromide, iodide, sulphate, phosphate, methanesulphonate, nitrate, maleate, acetate, benzoate, citrate, salicylate, trifluoroacetate, fumarate, tartrate, oxalate, succinate, ethanedisulphonate, benzoate and p-toluenesulphonate,
m denotes 1 or 2,
optionally in the form of the tautomers, mixtures of the tautomers, hydrates or solvates thereof.

In an embodiment enantiomerically pure compounds of formula 1, are as follows:
n denotes 2 or 3
X denotes $CH_2$, CO, $NR^2$, S or O;
B denotes a double-bonded group of formula $CR^3R^4$—O;
$R^1$ denotes H, methyl, ethyl, propyl, $CF_3$, $CH_2F$, $CH_2CF_3$, fluorine, chlorine, bromine, OH, methoxy, ethoxy, COOH or COOMe;
$R^2$ denotes H, methyl, ethyl or propyl;
$R^3$ denotes H or methyl;
$R^4$ denotes H or methyl;
$Y^{m-}$ denotes an anion with m negative charges, preferably an anion with m negative charges selected from among chloride, bromide, iodide, sulphate, phosphate, methanesulphonate, nitrate, maleate, acetate, benzoate, citrate, salicylate, trifluoroacetate, fumarate, tartrate, oxalate, succinate, ethanedisulphonate, benzoate and p-toluenesulphonate,
m denotes 1 or 2,
optionally in the form of the tautomers, mixtures of the tautomers, hydrates or solvates thereof.

In an additional embodiment enantiomerically pure compounds of formula 1, are as follows:
n denotes 2 or 3
X denotes $CH_2$, CO, $NR^2$, S or O;
B denotes a double-bonded group of formula $CH_2$—O;
$R^1$ denotes H, methyl, ethyl, propyl, $CF_3$, $CH_2F$, $CH_2CF_3$, fluorine, chlorine, bromine, OH, methoxy, ethoxy, COOH or COOMe;
$R^2$ denotes H, methyl, ethyl or propyl;
$Y^{m-}$ denotes an anion with m negative charges, preferably an anion with m negative charges selected from among chloride, bromide, iodide, sulphate, phosphate, methanesulphonate, nitrate, maleate, acetate, benzoate, citrate, salicylate, trifluoroacetate, fumarate, tartrate, oxalate, succinate, ethanedisulphonate, benzoate and p-toluenesulphonate,
m denotes 1 or 2,
optionally in the form of the tautomers, mixtures of the tautomers, hydrates or solvates thereof.

In an embodiment enantiomerically pure compounds of formula 1, are as follows:
n denotes 2 or 3
X denotes $NR^2$ or O;
B denotes a double-bonded group of formula $CH_2$—O;
$R^1$ denotes H, methyl, ethyl, propyl, $CF_3$, $CH_2F$ or $CH_2CF_3$;
$R^2$ denotes H, methyl, ethyl or propyl;
$Y^{m-}$ denotes an anion with m negative charges, preferably an anion with m negative charges selected from among chloride, bromide, iodide, sulphate, phosphate, methanesulphonate, nitrate, maleate, acetate, benzoate, citrate, salicylate, trifluoroacetate, fumarate, tartrate, oxalate, succinate, ethanedisulphonate, benzoate and p-toluenesulphonate,
m denotes 1 or 2,
optionally in the form of the tautomers, mixtures of the tautomers, hydrates or solvates thereof.

In another embodiment enantiomerically pure compounds of formula 1, are as follows:

n denotes 2

X denotes NH;

B denotes a double-bonded group of formula $CH_2$—O;

$R^1$ denotes H, methyl or $CF_3$;

$Y^{m-}$ denotes an anion with m negative charges, preferably an anion with m negative charges selected from among chloride, bromide, iodide, sulphate, phosphate, methanesulphonate, nitrate, maleate, acetate, benzoate, citrate, salicylate, trifluoroacetate, fumarate, tartrate, oxalate, succinate, ethanedisulphonate, benzoate and p-toluenesulphonate, m denotes 1 or 2, optionally in the form of the tautomers, mixtures of the tautomers, hydrates or solvates thereof.

In another embodiment enantiomerically pure compounds of formula 1, are presented wherein n=2 denotes and X, B, $R^1$, $R^2$, m and $Y^{m-}$ may have the meaning given hereinbefore, optionally in the form of the tautomers, mixtures of the tautomers, hydrates or solvates thereof.

In an embodiment enantiomerically pure compounds of formula 1, wherein X=$NR^2$ and n, X, B, $R^1$, $R^2$, m and $Y^{m-}$ may have the meaning given hereinbefore, optionally in the form of the tautomers, mixtures of the tautomers, hydrates or solvates thereof.

In an embodiment enantiomerically pure compounds of formula 1, wherein X=NH and n, X, B, $R^1$, m and $Y^{m-}$ may have the meaning given hereinbefore, optionally in the form of the tautomers, mixtures of the tautomers, hydrates or solvates thereof.

In another embodiment enantiomerically pure compounds of formula 1, wherein B denotes a double-bonded group of formula $CH_2$—O and n, X, $R^1$, $R^2$, m and $Y^{m-}$ may have the meaning given hereinbefore, optionally in the form of the tautomers, mixtures of the tautomers, hydrates or solvates thereof.

Compounds of the above formula 1 may be selected from but are not limited to the following:

R-8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one maleate R-8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one maleate R-8-{2-[1,1-dimethyl-4-(2-oxo-benzoxazol-3-yl)-butylamino]-1-hydroxy-ethyl}-6-hydroxy-4H-benzo[1,4]oxazin-3-one maleate R-8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one maleate R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one maleate R-8-{2-[1,1-dimethyl-4-(2-oxo-2,3-dihydro-benzimidazol-1-yl)-butylamino]-1-hydroxy-ethyl}-6-hydroxy-4H-benzo[1,4]oxazin-3-one maleate R-8-{2-[1,1-dimethyl-3-(2-oxo-benzoxazol-3-yl)-propylamino]-1-hydroxy-ethyl}-6-hydroxy-4H-benzo[1,4]oxazin-3-one maleate R-6-hydroxy-8-{1-hydroxy-2-[4-(4-methoxy-2-oxo-2,3-dihydro-benzimidazol-1-yl)-1,1-dimethyl-butylamino]-ethyl}-4H-benzo[1,4]oxazin-3-one maleate R-6-hydroxy-8-{1-hydroxy-2-[4-(5-methoxy-3-methyl-2-oxo-2,3-dihydro-benzimidazol-1-yl)-1,1-dimethyl-butylamino]-ethyl}-4H-benzo[1,4]oxazin-3-one maleate R-8-{2-[4-(6-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one maleate R-8-{2-[4-(7-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one maleate R-8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one tartrate R-8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one tartrate R-8-{2-[1,1-dimethyl-4-(2-oxo-benzoxazol-3-yl)-butylamino]-1-hydroxy-ethyl}-6-hydroxy-4H-benzo[1,4]oxazin-3-one tartrate R-8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one tartrate R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one tartrate R-8-{2-[1,1-dimethyl-4-(2-oxo-2,3-dihydro-benzimidazol-1-yl)-butylamino]-1-hydroxy-ethyl}-6-hydroxy-4H-benzo[1,4]oxazin-3-one tartrate R-8-{2-[1,1-dimethyl-3-(2-oxo-benzoxazol-3-yl)-propylamino]-1-hydroxy-ethyl}-6-hydroxy-4H-benzo[1,4]oxazin-3-one tartrate R-6-hydroxy-8-{1-hydroxy-2-[4-(4-methoxy-2-oxo-2,3-dihydro-benzimidazol-1-yl)-1,1-dimethyl-butylamino]-ethyl}-4H-benzo[1,4]oxazin-3-one tartrate R-6-hydroxy-8-{1-hydroxy-2-[4-(5-methoxy-3-methyl-2-oxo-2,3-dihydro-benzimidazol-1-yl)-1,1-dimethyl-butylamino]-ethyl}-4H-benzo[1,4]oxazin-3-one tartrate R-8-{2-[4-(6-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one tartrate R-8-{2-[4-(7-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one tartrate R-8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one hemi-ethanedisulphonate R-8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one hemi-ethanedisulphonate R-8-{2-[1,1-dimethyl-4-(2-oxo-benzoxazol-3-yl)-butylamino]-1-hydroxy-ethyl}-6-hydroxy-4H-benzo[1,4]oxazin-3-one hemi-ethanedisulphonate R-8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one hemi-ethanedisulphonate R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one hemi-ethanedisulphonate R-8-{2-[1,1-dimethyl-4-(2-oxo-2,3-dihydro-benzimidazol-1-yl)-butylamino]-1-hydroxy-ethyl}-6-hydroxy-4H-benzo[1,4]oxazin-3-one hemi-ethanedisulphonate R-8-{2-[1,1-dimethyl-3-(2-oxo-benzoxazol-3-yl)-propylamino]-1-hydroxy-ethyl}-6-hydroxy-4H-benzo[1,4]oxazin-3-one hemi-ethanedisulphonate R-6-hydroxy-8-{1-hydroxy-2-[4-(4-methoxy-2-oxo-2,3-dihydro-benzimidazol-1-yl)-1,1-dimethyl-butylamino]-ethyl}-4H-benzo[1,4]oxazin-3-one hemi-ethanedisulphonate R-6-hydroxy-8-{1-hydroxy-2-[4-(5-methoxy-3-methyl-2-oxo-2,3-dihydro-benzimidazol-1-yl)-1,1-dimethyl-butylamino]-ethyl}-4H-benzo[1,4]oxazin-3-one hemi-ethanedisulphonate R-8-{2-[4-(6-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one hemi-ethanedisulphonate R-8-{2-[4-(7-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one hemi-ethanedisulphonate optionally in the form of the tautomers, mixtures of the tautomers, hydrates or solvates thereof.

Additionally, compounds of the above formula 1 may be selected from but are not limited to the following:

R-8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one maleate R-8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one maleate R-8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one maleate R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one maleate R-8-{2-[1,1-dimethyl-3-(2-oxo-benzoxazol-3-yl)-propylamino]-1-hydroxy-ethyl}-6-hydroxy-4H-benzo[1,4]oxazin-3-one maleate R-8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one tartrate R-8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one tartrate R-8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one tartrate R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one tartrate R-8-{2-[1,1-dimethyl-3-(2-oxo-benzoxazol-3-yl)-propylamino]-1-hydroxy-ethyl}-6-hydroxy-4H-benzo[1,4]oxazin-3-one tartrate R-8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one hemi-ethanedisulphonate R-8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one hemi-ethanedisulphonate R-8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one hemi-ethanedisulphonate R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one hemi-ethanedisulphonate R-8-{2-[1,1-dimethyl-3-(2-oxo-benzoxazol-3-yl)-propylamino]-1-hydroxy-ethyl}-6-hydroxy-4H-benzo[1,4]oxazin-3-one hemi-ethanedisulphonate, optionally in the form of the tautomers, mixtures of the tautomers, hydrates or solvates thereof.

Compounds of the above formula 1 may be selected from but are limited to the following:

R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one maleate R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one tartrate R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one hemi-ethanedisulphonate, optionally in the form of the tautomers, mixtures of the tautomers, hydrates or solvates thereof.

Enantiomerically pure compounds of general formula 1 are found in crystalline form, optionally in the form of the crystalline tautomers, crystalline hydrates or crystalline solvates thereof Examples include the above enantiomerically pure, crystalline compounds of general formula 1, optionally in the form of the crystalline tautomers, crystalline hydrates or crystalline solvates thereof, which are further characterised in that they are crystalline compounds which are present in only a single crystal modification.

By the term a single crystal modification are meant crystalline compounds of formula 1 which do not constitute a mixture of any crystal modifications which may exist. The compounds of formula 1 according to the invention are characterised by their versatility of use in the therapeutic field. The compounds according to formula 1 are used due to their pharmaceutical activity as betamimetics.

In another aspect the present invention correspondingly relates to the above-mentioned enantiomerically pure compounds of formula 1 as pharmaceutical compositions. The present invention further relates to the use of the above-mentioned compounds of general formula 1 for preparing a pharmaceutical composition for the treatment of respiratory complaints. The present invention relates to the use of the above-mentioned compounds of general formula 1 for preparing a pharmaceutical composition for the treatment of respiratory complaints, which are selected from among obstructive pulmonary diseases of various origins, pulmonary emphysema of various origins, restrictive pulmonary diseases, interstitial pulmonary diseases, cystic fibrosis, bronchitis of various origins, bronchiectasis, ARDS (adult respiratory distress syndrome) and all forms of pulmonary oedema.

The compounds of formula 1 are used to prepare a pharmaceutical composition for the treatment of obstructive pulmonary diseases selected from among COPD (chronic obstructive pulmonary disease), bronchial asthma, paediatric asthma, severe asthma, acute asthma attacks and chronic bronchitis, one example according to the invention is to use the compounds of formula 1 for preparing a pharmaceutical composition for the treatment of bronchial asthma.

In another nonlimiting example, the compounds of formula 1 are used to prepare a pharmaceutical composition for the treatment of pulmonary emphysema which has its origins in COPD (chronic obstructive pulmonary disease) or α1-proteinase inhibitor deficiency.

In addition, the compounds of formula 1 may be used to prepare a pharmaceutical composition for the treatment of restrictive pulmonary diseases selected from among allergic alveolitis, restrictive pulmonary diseases triggered by work-related noxious substances, such as asbestosis or silicosis, and restriction caused by lung tumours, such as for example lymphangiosis carcinomatosa, bronchoalveolar carcinoma and lymphomas.

also In an additional nonlimiting example, the compounds of formula 1 are used to prepare a pharmaceutical composition for the treatment of interstitial pulmonary diseases selected from among pneumonia caused by infections, such as for example infection by viruses, bacteria, fungi, protozoa, helminths or other pathogens, pneumonitis caused by various factors, such as for example aspiration and left heart insufficiency, radiation-induced pneumonitis or fibrosis, collagenoses, such as for example lupus erythematodes, systemic sclerodermy or sarcoidosis, granulomatoses, such as for example Boeck's disease, idiopathic interstitial pneumonia or idiopathic pulmonary fibrosis (IPF).

The compounds of general formula 1 may be used to prepare a pharmaceutical composition for the treatment of cystic fibrosis or mucoviscidosis.

also In addition, the compounds of general formula 1 may be used to prepare a pharmaceutical composition for the treatment of bronchitis, such as for example bronchitis caused by bacterial or viral infection, allergic bronchitis and toxic bronchitis.

also In another nonlimiting embodiment, the compounds of general formula 1 are used to prepare a pharmaceutical composition for the treatment of bronchiectasis.

Another example includes, the compounds of general formula 1 being used to prepare a pharmaceutical composition for the treatment of ARDS (adult respiratory distress syndrome).

As an example, the compounds of general formula 1 may be used to prepare a pharmaceutical composition for the treatment of pulmonary edema, for example toxic pulmonary oedema after aspiration or inhalation of toxic substances and foreign substances.

As an additional embodiment the use of the compounds of formula 1 include preparing a pharmaceutical composition for the treatment of asthma or COPD. Also of particular importance is the above-mentioned use of compounds of formula 1 for preparing a pharmaceutical composition for once-a-day treatment of inflammatory and obstructive respiratory complaints, particularly for the once-a-day treatment of asthma or COPD.

The present invention also relates to a process for the treatment of the above-mentioned diseases, characterised in that one or more of the above-mentioned compounds of general formula 1 are administered in therapeutically effective amounts. The present invention further relates to processes for the treatment of asthma or COPD, characterised in that one or more of the above-mentioned compounds of general formula 1 are administered once a day in therapeutically effective amounts.

TERMS AND DEFINITIONS USED

By the term "$C_{1-6}$-alkyl" (including those which are part of other groups) are meant branched and unbranched alkyl groups with 1 to 6 carbon atoms and by the term "$C_{1-4}$-alkyl" are meant branched and unbranched alkyl groups with 1 to 4 carbon atoms. Alkyl groups with 1 to 4 carbon atoms are preferred. Examples of these include but are not limited to: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc. may optionally also be used for the above-mentioned groups. Unless otherwise stated, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{2-6}$-alkenyl" (including those which are part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they have at least one double bond. Alkenyl groups with 2 to 4 carbon atoms are preferred. Nonlimiting examples of these include: ethenyl or vinyl, propenyl, butenyl, pentenyl, or hexenyl. Unless otherwise stated, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred. Examples of these include: ethynyl, propynyl, butynyl, pentynyl, or hexynyl. Unless otherwise stated, the definitions propynyl, butynyl, pentynyl and hexynyl include all the possible isomeric forms of the groups in question. Thus, for example, propynyl includes 1-propynyl and 2-propynyl, butynyl includes 1, 2- and 3-butynyl, 1-methyl-1-propynyl, 1-methyl-2-propynyl etc.

By the term "$C_{3-6}$-cycloalkyl" (including those which are part of other groups) are meant cyclic alkyl groups with 3 to 6 carbon atoms. Examples of these include: cyclopropyl, cyclobutyl, cyclopentyl or cyclohexyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{1-6}$-haloalkyl" (including those which are part of other groups) are meant branched and unbranched alkyl groups with 1 to 6 carbon atoms, which are substituted by one or more halogen atoms. By the term "$C_{1-4}$-alkyl" are meant branched and unbranched alkyl groups with 1 to 4 carbon atoms, which are substituted by one or more halogen atoms. Alkyl groups with 1 to 4 carbon atoms are preferred. Examples of these include: $CF_3$, $CHF_2$, $CH_2F$, $CH_2CF_3$.

By the term "aryl" (including those which are part of other groups) are meant aromatic ring systems with 6 or 10 carbon atoms. Examples of these include: phenyl or naphthyl, the preferred aryl group being phenyl. Unless otherwise stated, the aromatic groups may be substituted by one or more groups selected from among methyl, ethyl, iso-propyl, tert-butyl, hydroxy, fluorine, chlorine, bromine and iodine.

Halogen within the scope of the present invention denotes fluorine, chlorine, bromine or iodine. Unless stated to the contrary, fluorine, chlorine and bromine are the preferred halogens.

The term enantiomerically pure describes within the scope of the present invention compounds of formula 1 which are present in an enantiomerical purity of at least 85% ee, preferably at least 90% ee, particularly preferably $\geq$95% ee. The term ee (enantiomeric excess) is known in the art and describes the optical purity of chiral compounds.

The compounds according to the invention may be prepared by the method outlined in Scheme 1.

EXAMPLES

Synthesis of Intermediate Stages

Intermediate 1: tert-butyl (3-amino-3-methyl-butyl)-carbamate: 23.6 g (117 mmol) tert-butyl (1,1-dimethyl-3-oxo-propyl)-carbamate in 700 mL ethanolic ammonia solution are treated in the presence of 3.5 g Raney nickel at ambient temperature with 3 bar hydrogen pressure until no more educt can be detected by thin layer chromatography. The catalyst is filtered off and the solvent is eliminated by distillation.

Yield: 22.7 g (96%); mass spectroscopy: [M+H]$^+$=203.

Intermediate 2: 1-(3-amino-1,1-dimethyl-proypl)-6-methyl-1,3-dihydro-benzimidazol-2-one

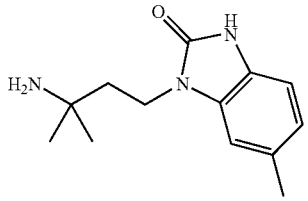

a) tert-butyl [3-methyl-3-(5-methyl-2-nitro-phenylamino)-butyl]-carbamate: 2.0 g (12.9 mmol) 3-fluoro-4-nitro-toluene, 2.6 g (13.0 mmol) tert-butyl (3-amino-3-methyl-butyl)-carbamate and 2.3 g (16.8 mmol) potassium carbonate are stirred overnight at ambient temperature in 20 mL DMF. The solvent is distilled off and the residue is combined with ethyl acetate. The mixture is washed repeatedly with water, dried with sodium sulphate and the solvent is eliminated.

Yield 4.8 g, mass spectroscopy: [M+H]$^+$=338.

b) tert-butyl [3-(2-amino-5-methyl-phenylamino)-3-methyl-butyl]-carbamate: 4.71 g (14.0 mmol) tert-butyl [3-methyl-3-(5-methyl-2-nitro-phenylamino)-butyl]-carbamate are dissolved in 110 mL methanol and hydrogenated in the presence of 340 mg palladium on charcoal (10%) at ambient temperature. Then the catalyst is separated off and the solvent is distilled off. Yield: 3.72 g (87%); mass spectroscopy: [M+H]$^+$=308.

c) tert-butyl [3-methyl-3-(6-methyl-2-oxo-2,3-dihydro-benzimidazol-1-yl)-butyl]-carbamate: 1.76 g (5.7 mmol) tert-butyl [3-(2-amino-5-methyl-phenylamino)-3-methyl-butyl]-carbamate are dissolved in 35 mL THF, combined with 2.1 g (12.7 mmol) 1,1'-carbonyldi-(1,2,4-triazole) and stirred overnight. The solvent is distilled off and the residue is dissolved in ethyl acetate. The solution is washed successively with potassium hydrogen sulphate solution and sodium chloride solution and dried with sodium sulphate. The residue is chromatographed (silica gel; dichloromethane with 0-16% methanol:ammonia=9:1) and the crude product thus obtained is stirred with diethyl ether.

Yield: 1.12 g (59%); mass spectroscopy: [M+H]$^+$=334.

d) 1-(3-amino-1,1-dimethyl-proypl)-6-methyl-1,3-dihydro-benzimidazol-2-one: A solution of 1.50 g (4.5 mmol) tert-butyl [3-methyl-3-(6-methyl-2-oxo-2,3-dihydro-benzimidazol-1-yl)-butyl]-carbamate in 100 mL dioxane is combined with 10 mL of 4 molar hydrochloric acid in dioxane and then heated to 90° C. for 90 minutes, during which time a white precipitate is formed. After cooling to ambient temperature the solvent is distilled off and the residue is stirred in diethyl ether.

Yield: 1.04 g (86%; hydrochloride); mass spectroscopy: [M+H]$^+$=234.

Intermediate 3: 1-(3-amino-3-methyl-butyl)-5-trifluoromethyl-1,3-dihydro-benzimidazol-2-one

a) tert-butyl [3-methyl-3-(2-nitro-4-trifluoromethyl-phenylamino)-butyl]-carbamate: is prepared analogously to Method 2a) from a total of 3.25 g (15.5 mmol) 1-fluoro-2-nitro-4-trifluoromethyl-benzene and 2.74 g (13.5 mmol) tert-butyl (3-amino-3-methyl-butyl)-carbamate.

Yield: 6.1 g, mass spectroscopy: [M+H]$^+$=392.

b) tert-butyl [3-(2-amino-4-trifluoromethyl-phenylamino)-1,1-dimethyl-propyl]-carbamate: 6.10 g (15.6 mmol) tert-butyl [3-methyl-3-(2-nitro-4-trifluoromethyl-phenylamino)-butyl]-carbamate are hydrogenated analogously to Method 2b).

Yield: 5.05 g (90%); mass spectroscopy: [M+H]$^+$=362.

c) tert-butyl [1,1-dimethyl-3-(2-oxo-5-trifluoromethyl-2,3-dihydro-benzimidazol-1-yl)-propyl]-carbamate: 5.00 g (13.8 mmol) tert-butyl [3-(2-amino-4-trifluoromethyl-phenylamino)-1,1-dimethyl-propyl]-carbamate and 6.73 g (41.5 mmol) 1,1'-carbonyldiimidazole are reacted and worked up analogously to Method 2c).

Yield: 4.18 g (78%); mass spectroscopy: [M−H]$^-$=386.

d) 1-(3-amino-3-methyl-butyl)-5-trifluoromethyl-1,3-dihydro-benzimidazol-2-one: method of preparation is analogously to Method 2d) from 2.89 g (7.5 mmol) tert-butyl [1,1-dimethyl-3-(2-oxo-5-trifluoromethyl-2,3-dihydro-benzimidazol-1-yl)-propyl]-carbamate.

Yield: 1.60 g (66%; hydrochloride); mass spectroscopy: [M+H]$^+$=288

Intermediate 4: 3-(3-amino-3-methyl-butyl)-3H-benzoxazol-2-one

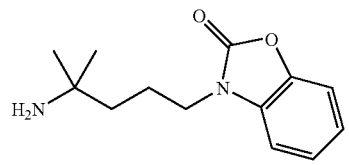

a) 1-iodo-4-methyl-nitro-pentane: A solution of 44.7 mL (352 mmol) chlorotrimethylsilane and 50 mL acetonitrile is added dropwise to 26.0 g (177 mmol) 1-methyl-4-nitro-pentan-1-ol and 52.8 g (352 mmol) sodium iodide in 350 mL acetonitrile. Then the mixture is heated to 50° C. for 4 hours, then the solvent is distilled off and the residue is combined with 500 mL diethyl ether. It is washed successively with water, sodium thiosulphate solution and sodium chloride solution. The organic phase is dried with sodium sulphate and evaporated down. Yield: 34.2 g.

b) 3-(3-methyl-3-nitro-butyl)-3H-benzoxazol-2-one: 1.70 g (42.5 mmol) sodium hydride (60%) are added batchwise to a solution of 4.50 g (33.3 mmol) benzoxazol-2-one in 50 mL DMF, while the temperature is kept below 0° C. by cooling. After one hour's stirring a solution of 9.61 g (37.4 mmol) 1-iodo-4-methyl-4-nitro-pentane in 20 mL DMF is added dropwise such that the temperature does not rise above 5° C. The mixture is left overnight at ambient temperature with stirring and the solvent is distilled off. The residue is taken up in ethyl acetate and washed successively with water and sodium chloride solution, dried with sodium sulphate and evaporated down. 11.0 g product are obtained. Mass spectroscopy: [M+H]⁺=265.

c) 3-(3-amino-3-methyl-butyl)-3H-benzoxazol-2-one: 11.0 g 3-(3-methyl-3-nitro-butyl)-3H-benzoxazol-2-one from the reaction described above are dissolved in 130 mL ethanol and hydrogenated with Raney nickel as catalyst at 5 bar for 20 hours. The catalyst is filtered off and the filtrate is freed from the solvent. 10% ethanolic hydrochloric acid is added, the solvent is distilled off and the residue is stirred in an acetone/diethyl ether mixture.

Yield: 6.0 g (77% over 2 steps, hydrochloride); melting range=145-147° C.

Intermediate 5: 3-(3-amino-3-methyl-butyl)-3H-benzoxazol-2-one

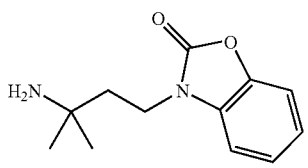

a) tert-butyl [1,1-dimethyl-3-(2-oxo-benzoxazol-3-yl)-propyl]-carbamate: 4.0 g (29.6 mmol) benzoxazol-2-one are dissolved in 40 mL DMPU and cooled with an ice bath. Under protective gas 897 mg (95%; 35.5 mmol) sodium hydride is added batchwise to this solution. The reaction mixture is heated to ambient temperature and then stirred for another hour. 9.85 g (44.4 mmol) tert-butyl (3-amino-1,1-dimethyl-propyl)-carbamate and 1.97 g (5.3 mmol) tetrabutylammonium iodide are added and the mixture is stirred overnight. The reaction is stopped by the careful addition of sodium hydrogen carbonate solution. Ethyl acetate is added, the aqueous phase is separated off and extracted repeatedly with ethyl acetate. The combined organic phases are washed with sodium chloride solution, dried with sodium sulphate and evaporated down. Purification of the residue by column chromatography (silica gel; petroleum ether/ethyl acetate=7:3) yields the desired product.

Yield 4.1 g (43%); mass spectroscopy: [M+H]⁺=321.

b) 3-(3-amino-3-methyl-butyl)-3H-benzoxazol-2-one: 18 mL trifluoroacetic acid are added dropwise at ambient temperature to a solution of 4.0 g (12.5 mmol) tert-butyl [1,1-dimethyl-3-(2-oxo-benzoxazol-3-yl)-propyl]-carbamate in 110 mL dichloromethane. The mixture is left overnight with stirring and then the solvent is dissolved off. The oil remaining is stirred into diethyl ether, during which time a solid is precipitated, which is filtered off. After further stirring with diethyl ether and filtration the product is obtained.

Yield: 3.63 g (65%; trifluoroacetate); mass spectroscopy: [M+H]⁻=221.

Intermediate 6: 1-(3-amino-3-methyl-butyl)-4-methoxy-1,3-dihydro-benzimidazol-2-one

a) 4-methyl-4-nitro-pentan-1-ol: 50 g (0.285 mol) methyl 4-methyl-4-nitro-pentanoate are dissolved in a 6:4 mixture of THF/ethanol (1000 mL). The solution is cooled to −10° C. and combined with 24.2 g (0.571 mol) lithium chloride. Then 21.6 g (0.571 mol) lithium borohydride are added batchwise. The mixture is stirred for 30 minutes at −10° C. and then heated overnight to ambient temperature. The reaction mixture is stirred for 6 hours at 60° C. and overnight at ambient temperature. It is mixed with water and adjusted to pH 6 with dilute hydrochloric acid. The solvent is distilled off and the residue is combined with water. It is extracted with dichloromethane, the combined organic phases are washed with water and ammonium chloride solution and dried with sodium sulphate. After elimination of the solvent the product is obtained.

Yield: 40.0 g (95%); mass spectroscopy: [M+H]⁺=148.

b) 1-iodo-4-methyl-4-nitro-pentane: 70 mL (0.544 mol) trimethylchlorosilane are added dropwise at ambient temperature to 40 g (0.272 mol) 4-methyl-4-nitro-pentan-1-ol and 81.5 g (0.544 mol) sodium iodide in 350 mL acetonitrile. The reaction mixture is filtered, evaporated down and combined with diethyl ether. The organic phase is washed with sodium bisulphite solution and water, dried and freed from the solvent.

Yield: 56.0 g (80%); mass spectroscopy: [M−NO₂]⁺=211.

c) 2-methoxy-6-nitro-phenylamine: 85% potassium hydroxide solution (11.7 g, 0.179 mol) is added to a solution of 25 g (0.162 mol) 2-amino-3-nitro-phenol in 200 mL DMF. Then 11.1 mL (0.178 mol) iodomethane are added dropwise and the mixture is stirred overnight at ambient temperature. The reaction mixture is poured onto ice and stirred for one hour. The precipitated product is filtered off, washed with water and dried.

Yield: 23.8 g (87%); mass spectroscopy: [M+H]⁺=169.

d) ethyl(2-methoxy-6-nitro-phenyl)-carbamate: At reflux temperature 17.1 mL (0.141 mol) trichloromethylchloroformate are added dropwise to a solution of 23.8 g (0.142 mol) 2-methoxy-6-nitro-phenylamine in 300 mL THF and then the mixture is stirred for 4 hours at this temperature. The solvent is distilled off and the residue is stirred with isopropanol, whereupon a yellow solid is precipitated.

Yield: 25.0 g (73%); mass spectroscopy: [M+H]⁺=241.

e) ethyl(2-amino-6-methoxy-phenyl)-carbamate: 25.0 g (0.104 mol) ethyl(2-methoxy-6-nitro-phenyl)-carbamate are dissolved in 400 mL methanol. 116.4 g (0.516 mol) SnCl₂ 2H₂O are added and the mixture is refluxed for 3 hours. The reaction mixture is evaporated down, combined with sodium carbonate solution and filtered. The aqueous phase is repeatedly extracted with dichloromethane and the combined organic phases are washed with sodium chloride solution, dried and evaporated down. The residue that crystallises out on standing is stirred with isopropanol.

Yield: 13.0 g (59%); mass spectroscopy: [M+H]⁺=211.

f) ethyl 7-methoxy-2-oxo-2,3-dihydro-benzimidazol-1-carboxylate: 13.0 g (0.062 mol) ethyl(2-amino-6-methoxy-phenyl)-carbamate and 10.3 mL (0.074 mol) triethylamine in 100 mL dichloromethane are added, while cooling with ice, to a solution of 8.20 mL (0.068 mol) trichloromethylchloroformate in 50 mL dichloromethane. After 4 hours stirring at ambient temperature the reaction mixture is poured onto ice and extracted with dichloromethane. The combined organic phases are washed with water, dried and freed from the solvent. The residue is stirred in diethyl ether.

Yield: 9.0 g (62%); mass spectroscopy: [M+H]⁺=237.

g) 4-methoxy-1-(3-methyl-3-nitro-butyl)-1,3-dihydro-benzimidazol-2-one: 4.0 g (17 mmol) ethyl 7-methoxy-2-oxo-2,3-dihydro-benzimidazol-1-carboxylate in DMF are combined with 85% potassium hydroxide solution (3.3 g, 51 mmol) while cooling with the ice bath. After 30 minutes a solution of 5.2 g (21 mmol) 1-iodo-4-methyl-4-nitro-pentane in DMF is added and the mixture is stirred overnight at ambient temperature. The reaction mixture is diluted with water and extracted with ethyl acetate. The combined organic phases are washed with water, dried and freed from the solvent. The oil remaining is purified by chromatography on a silica gel column (cyclohexane/ethyl acetate gradient).

Yield: 0.5 g (8%); mass spectroscopy: [M+H]⁺=366.

h) 1-(3-amino-3-methyl-butyl)-4-methoxy-1,3-dihydro-benzimidazol-2-one: 1.4 g (4.8 mmol) 4-methoxy-1-(3-methyl-3-nitro-butyl)-1,3-dihydro-benzimidazol-2-one are dissolved in methanol and hydrogenated at 3 bar in the presence of Raney nickel. The catalyst is separated off, the solvent is distilled off and the residue is dissolved in ethanolic hydrochloric acid. The solvents are removed by distillation and the solid remaining is stirred with isopropanol.

Yield: 0.6 g (42%, hydrochloride); mass spectroscopy: [M+H]⁺=300.

Intermediate 7: 1-(3-amino-3-methyl-butyl)-5-methoxy-3-methyl-1,3-dihydro-benzimidazol-2-one

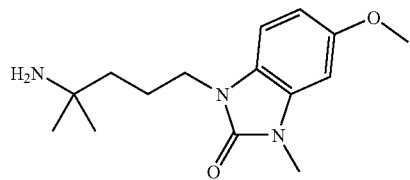

a) (5-methoxy-2-nitro-phenyl)-methyl-amine: 83.5 mL (167.0 mmol) of a 2 molar solution of methylamine in THF are added dropwise to 14.3 g (83.56 mmol) 3-fluoro-4-nitroanisol and 12.71 g (92.02 mmol) potassium carbonate in 200 mL dichloromethane. The mixture is stirred overnight and then water is added. The organic phase is washed successively with water and ammonium chloride solution, dried and evaporated down. The product remaining is stirred with hexane.

Yield: 12.7 g (84%); mass spectroscopy: [M+H]⁺=183.

b) 4-methoxy-N-2-methyl-benzene-1,2-diamine: 12.5 g (68.6 mmol) (5-methoxy-2-nitro-phenyl)-methyl-amine and 77.39 g (343.0 mmol) SnCl₂ 2H₂O in 200 mL ethanol are refluxed for 6 hours. The reaction mixture is washed with sodium carbonate solution, filtered and evaporated down. The residue is combined with water and extracted with ethyl acetate. The combined organic phases are washed with water, dried and freed from the solvent. Yield: 8.0 g (77%); mass spectroscopy: [M+H]⁺=153.

c) 5-methoxy-1-methyl-1,3-dihydro-benzimidazol-2-one: 8.0 g (52.56 mmol) 4-methoxy-N-2-methyl-benzene-1,2-diamine and 8.7 mL (63.00 mmol) triethylamine are dissolved in 100 mL dichloromethane and added dropwise to 7 mL (58.00 mmol) trichloromethylchloroformate in 50 mL dichloromethane. The reaction mixture is stirred overnight at ambient temperature, then poured into ice water and extracted with dichloromethane. The combined organic phases are washed with water, dried and evaporated down. The product remaining is stirred with diethyl ether.

Yield: 4.2 g (45%); mass spectroscopy: [M+H]⁺=179.

d) 5-methoxy-3-methyl-1-(3-methyl-3-nitro-butyl)-1,3-dihydro-benzimidazol-2-one: 1.1 g (28 mmol) 60% sodium hydride are added to 2.5 g (14 mmol) 5-methoxy-1-methyl-1,3-dihydro-benzimidazol-2-one in 30 mL DMF while cooling with the ice bath. After 30 minutes a solution of 1-iodo-4-methyl-4-nitro-pentane in 20 mL DMF is piped in and the mixture is stirred overnight. It is diluted with water and extracted with ethyl acetate. The combined organic phases are washed with water, dried and evaporated down. The product remaining is stirred with diethyl ether.

Yield: 2.7 g (63%); mass spectroscopy: [M+H]⁺=308.

e) 1-(3-amino-3-methyl-butyl)-5-methoxy-3-methyl-1,3-dihydro-benzimidazol-2-one: 2.7 g (8.7 mmol) 5-methoxy-3-methyl-1-(3-methyl-3-nitro-butyl)-1,3-dihydro-benzimidazol-2-one and 9.93 g (44.0 mmol) SnCl₂ 2H₂O in 200 mL ethanol are refluxed for 3 hours. The reaction mixture is evaporated down, combined with sodium carbonate solution and filtered. The filtrate is extracted with ethyl acetate and the combined organic phases are washed with water, dried and freed from the solvent. The residue is dissolved in ethanol and the solution is combined with ethereal hydrochloric acid. After the solvent has been dissolved off the product remaining is stirred with diisopropylether.

Yield: 0.7 g (29%); mass spectroscopy: [M+H]⁺=278.

Intermediate 8: 3-(4-amino-4-methyl-pentyl)-5-fluoro-1-methyl-1,3-dihydro-benzimidazol-2-one

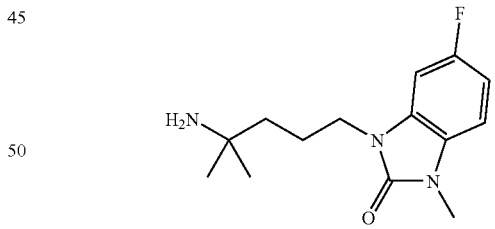

a) (4-fluoro-2-nitro-phenyl)-methyl-amine: 157 ml (314 mmol) of a 2 molar solution of methylamine in THF are added dropwise to 25 g (157 mmol) 2,4-difluoro-nitrobenzene and 23.9 g (173 mmol) potassium carbonate in 300 mL dichloromethane while being cooled. The mixture is stirred overnight at ambient temperature and then combined with water. The organic phase is washed with water, dried and evaporated down. The residue is stirred with diethyl ether. Yield: 18 g (69%); mass spectroscopy [M+H]⁺=171.

b) 4-fluoro-N-1-methyl-benzene-1,2-diamine: 22 g (0.12 mol) (4-fluoro-2-nitro-phenyl)-methyl-amine in 250 mL ethanol are hydrogenated at 4 bar hydrogen pressure with palladium on charcoal as catalyst. The catalyst is separated off and the solvent is distilled off. The oil remaining is purified by chromatography (silica gel, hexane/ethyl acetate gradient). Yield: 9 g (50%); mass spectroscopy [M+H]$^+$=141.

c) 5-fluoro-1-methyl-1,3-dihydro-benzimidazol-2-one: 13.0 g (92.1 mmol) 4-fluoro-N-1-methyl-benzene-1,2-diamine are reacted with trichloromethyl chloroformate analogously to the method described for Intermediate 7c. After stirring in diethyl ether the product is isolated. Yield: 6.0 g (39%); mass spectroscopy: [M+H]$^+$=167.

d) 5-fluoro-1-methyl-3-(4-methyl-4-nitro-pentyl)-1,3-dihydro-benzimidazol-2-one: First of all 0.624 g (13.9 mmol) 60% sodium hydride and then, while cooling, 4.6 g (17.8 mmol) 1-iodo-4-methyl-4-nitro-pentane in 10 mL DMF are added to a solution of 2.1 g (12.6 mmol) 5-fluoro-1-methyl-1,3-dihydro-benzimidazol-2-one in DMF. The reaction mixture is stirred overnight at ambient temperature, then poured onto water and extracted with diethyl ether. The organic phases are evaporated down and the residue is recrystallised from isopropylether. Yield: 1.8 g (48%); mass spectroscopy [M+H]$^+$=296.

e) 3-(4-amino-4-methyl-pentyl)-5-fluoro-1-methyl-1,3-dihydro-benzimidazol-2-one: 1.8 g (6.09 mmol) 5-fluoro-1-methyl-3-(4-methyl-4-nitro-pentyl)-1,3-dihydro-benzimidazol-2-one in 50 mL methanol are hydrogenated at 3 bar hydrogen pressure with Raney nickel as catalyst. The catalyst is separated off and the solvent is distilled off. In order to prepare the hydrochloride the residue is combined with ethanol and hydrochloric acid in diethyl ether.

Yield: 1.5 g (83%, hydrochloride); melting range=225-228° C.; mass spectroscopy [M+H]$^+$=303.

Intermediate 9: 3-(4-amino-4-methyl-pentyl)-4-fluoro-1-methyl-1,3-dihydro-benzimidazol-2-one

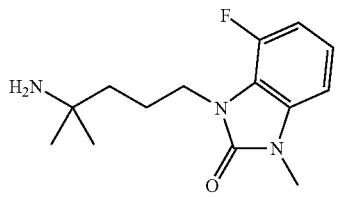

a) (3-fluoro-2-nitro-phenyl)-methyl-amine: Reaction of 2.0 g (2.6 mmol) 2,6-difluoro-nitrobenzene with a 2 molar solution of methylamine in THF analogously to the method for preparing Intermediate 7a. Yield: 1.8 g (86%); mass spectroscopy: [M+H]$^+$=171.

b) 3-fluoro-N-1-methyl-benzene-1,2-diamine: Reduction of 8.0 g (47.0 mmol) (3-fluoro-2-nitro-phenyl)-methyl-amine with SnCl$_2$×2H$_2$O according to the method described for Intermediate 7b. Yield: 4.5 g (68%); mass spectroscopy: [M+H]$^+$=141.

c) 4-fluoro-1-methyl-1,3-dihydro-benzimidazol-2-one: Prepared from 4.5 g (32.1 mmol) 3-fluoro-N-1-methyl-benzene-1,2-diamine analogously to the method described for Intermediate 7c. Yield: 1.4 g (26%); mass spectroscopy: [M+H]$^+$=167.

d) 4-fluoro-1-methyl-3-(4-methyl-4-nitro-pentyl)-1,3-dihydro-benzimidazol-2-one: Prepared from 1.4 g (8.42 mmol) 4-fluoro-1-methyl-1,3-dihydro-benzimidazol-2-one analogously to the method described for Intermediate 7d.

Yield: 1.7 g (68%); mass spectroscopy: [M+H]$^+$=296.

e) 3-(4-amino-4-methyl-pentyl)-4-fluoro-1-methyl-1,3-dihydro-benzimidazol-2-one: A solution of 2 g (6.7 mmol) 4-fluoro-1-methyl-3-(4-methyl-4-nitro-pentyl)-1,3-dihydro-benzimidazol-2-one in methanol is hydrogenated in the presence of Raney nickel at 3 bar hydrogen pressure. After separation of the catalyst hydrochloric acid in diethyl ether is added. The hydrochloride precipitated is filtered off and dried.

Yield: 1.5 g (83%, hydrochloride); melting range=230-232° C.; mass spectroscopy: [M+H]$^+$=303.

Intermediate 10: 6-benzyloxy-8-(R)-oxiranyl-4H-benzo[1,4]oxazin-3-one

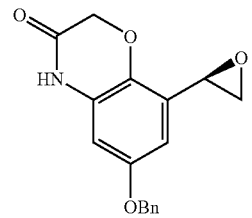

a) 1-(5-benzyloxy-2-hydroxy-3-nitro-phenyl)-ethanone: 18 mL fuming nitric acid are added dropwise to a solution of 81.5 g (0.34 mol) 1-(5-benzyloxy-2-hydroxy-phenyl)-ethanon in 700 mL acetic acid while cooling with the ice bath, such that the temperature does not rise above 20° C. Then the reaction mixture is stirred for two hours at ambient temperature, poured onto ice water and filtered. The product is recrystallised from isopropanol, suction filtered and washed with isopropanol and diisopropylether.

Yield: 69.6 g (72%); mass spectroscopy [M+H]$^+$=288.

b) 1-(3-amino-5-benzyloxy-2-hydroxy-phenyl)-ethanone: 69.5 g (242 mmol) of 1-(5-benzyloxy-2-hydroxy-3-nitro-phenyl)-ethanone are dissolved in 1.4 L methanol and hydrogenated at 3 bar and at ambient temperature in the presence of 14 g rhodium on charcoal (10%) as catalyst. Then the catalyst is filtered off and the filtrate is evaporated down. The residue is reacted further without any additional purification.

Yield: 60.0 g (96%), R$_f$ value=0.45 (dichloromethane on silica gel).

c) 8-acetyl-6-benzyloxy-4H-benzo[1,4]oxazin-3-one: 21.0 mL (258 mmol) chloroacetyl chloride are added dropwise to 60.0 g (233 mmol) 1-(3-amino-5-benzyloxy-2-hydroxy-phenyl)-ethanone and 70.0 g (506 mmol) potassium carbonate while cooling with the ice bath. Then the mixture is stirred overnight at ambient temperature and then for 6 hours at reflux temperature. The hot reaction mixture is filtered, then evaporated down to about 400 mL and combined with ice water. The precipitate formed is suction filtered, dried and purified chromatography on a short silica gel column (dichloromethane:methanol=99:1). The fractions containing the product are evaporated down, suspended in isopropanol/diisopropylether, suction filtered and washed with diisopropylether.

Yield: 34.6 g (50%); mass spectroscopy [M+H]$^+$=298.

d) 6-benzyloxy-8-(2-chloro-acetyl)-4H-benzo[1,4]oxazin-3-one: 13.8 g (46.0 mmol) 8-acetyl-6-benzyloxy-4H-benzo[1,4]oxazin-3-one and 35.3 g (101.5 mmol) benzyltrimethyl-ammonium-dichloriodate are stirred in 250 mL dichloroethane, 84 mL glacial acetic acid and 14 mL water for 5 hours at 65° C. After cooling to ambient temperature the mixture is combined with 5% sodium hydrogen sulphite solution and stirred for 30 minutes. The precipitated solid is suction filtered, washed with water and diethyl ether and dried.

Yield: 13.2 g (86%); mass spectroscopy [M+H]$^+$=330/32.

e) 6-benzyloxy-8-((R)-2-chloro-1-hydroxy-ethyl)-4H-benzo[1,4]-oxazin-3-one: This is carried out analogously to to a method described in the literature (Org. Lett. 2002, 4, 4373-4376). At −15° C. 8 mL of a mixture of formic acid and triethylamine (molar ratio=5:2) are added dropwise to 13.15 g (39.6 mmol) 6-benzyloxy-8-(2-chloro-acetyl)-4H-benzo[1,4]oxazin-3-one and 25.5 mg (0.04 mmol) Cp*RhCl[(S,S)-TsDPEN] (Cp*=pentamethylcyclopentadienyl and TsDPEN=(1S.2S)—N-p-toluenesulphonyl-1,2-diphenylethylenediamine) in 40 mL dimethylformamide. The mixture is left for 5 hours at this temperature with stirring, then 25 mg catalyst are added and the mixture is stirred overnight at −15° C. The reaction mixture is combined with ice water and filtered. The filter residue is dissolved in dichloromethane, dried with sodium sulphate and freed from the solvent. The residue is chromatographed (dichloromethane/methanol gradient) and the product is recrystallised from diethyl ether/diisopropylether.

Yield: 10.08 g (76%); $R_f$ value=0.28 (dichloromethane: methanol=50:1 on silica gel).

f) 6-benzyloxy-8-(R)-oxiranyl-4H-benzo[1,4]oxazin-3-one: 10.06 g (30.1 mmol) 6-benzyloxy-8-((R)-2-chloro-1-hydroxy-ethyl)-4H-benzo[1,4]-oxazin-3-one are dissolved in 200 mL dimethylformamide. The solution is combined at 0° C. with 40 mL of a 2 molar sodium hydroxide solution and stirred for 4 hours at this temperature. The reaction mixture is poured onto ice water, stirred for 15 minutes and then filtered. The solid is washed with water and dried. Yield: 8.60 g (96%); mass spectroscopy [M+H]$^+$=298.

Synthesis of Salt Precursors

General Method 1: 1 mmol glyoxal aldehyde or acetal and 1 mmol amine are stirred for 30 minutes in 5 mL tetrahydrofuran at 50° C. The mixture is cooled to 0° C. and under an argon atmosphere 1.5 mL of a 2 molar solution of lithium borohydride in tetrahydrofuran is added dropwise. The mixture is stirred for 30 min at 0° C., combined with 10 mL dichloromethane and 3 mL water, stirred for another hour at ambient temperature and then filtered through kieselguhr, while eluting with dichloromethane. The eluate is freed from the solvent and the residue is purified by chromatography, if necessary. The benzylether thus obtained is dissolved in methanol and hydrogenated with palladium on charcoal (10%) as catalyst at 2.5 bar and ambient temperature. Then the catalyst is separated off and the crude product is purified by chromatography (reverse phase, acetonitrile/water gradient with 0.1% trifluoroacetic acid) or recrystallised from acetonitrile.

General Method 2: 1 mmol glyoxal aldehyde or acetal and 1 mmol amine are suspended in 5 mL ethanol and heated to 70° C. The resulting solution is stirred for one hour at 70° C. and then cooled to ambient temperature. After the addition of 113 mg (3 mmol) sodium borohydride the mixture is stirred for 3 hours at ambient temperature, combined with 0.7 mL saturated potassium carbonate solution and stirred for a further 30 minutes. It is filtered through aluminium oxide (basic), washed repeatedly with dichloromethane/methanol 15:1, evaporated down and chromatographed (silica gel; dichloromethane with 0-10% methanol:ammonia=9:1). The benzyl compound thus obtained is dissolved in 10 mL methanol and hydrogenated with palladium on charcoal as catalyst at 1 bar hydrogen pressure. Then the catalyst is filtered off and the filtrate is evaporated down.

Salt precursor 1: 8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one

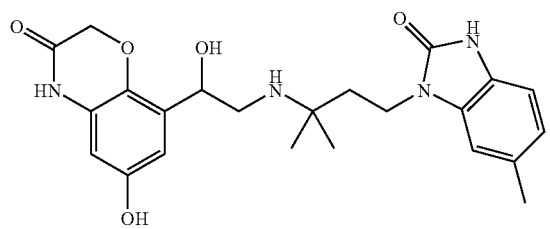

The compound is prepared according to General Method 1 from 357 mg (1 mmol) 6-benzyloxy-8-(2-ethoxy-1,2-dihydroxy-ethyl)-4H-benzo[1,4]oxazin-3-one and 233 mg (1 mmol) 1-(3-amino-3-methyl-butyl)-6-methyl-1,3-dihydro-benzimidazol-2-one.

Yield: 170 mg (31%, trifluoroacetate); mass spectroscopy: [M+H]$^+$=441.

Salt precursor 2: 8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one

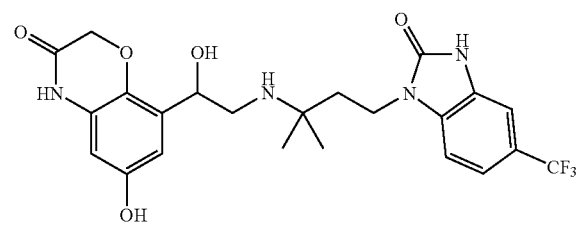

Prepared according to General Method 1 from 357 mg (1 mmol) 6-benzyloxy-8-(2-ethoxy-1,2-dihydroxy-ethyl)-4H-benzo[1,4]oxazin-3-one and 287 mg (1 mmol) 1-(3-amino-3-methyl-butyl)-5-trifluoromethyl-1,3-dihydro-benzimidazol-2-one.

Yield: 76 mg (13%, trifluoroacetate); mass spectroscopy: [M+H]$^-$=495.

Salt precursor 3: 8-{2-[1,1-dimethyl-4-(2-oxo-benzoxazol-3-yl)-butylamino]-1-hydroxy-ethyl}-6-hydroxy-4H-benzo[1,4]oxazin-3-one

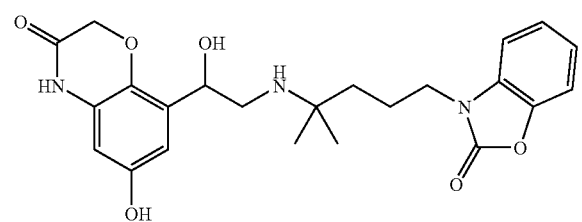

357 mg (1 mmol) 6-benzyloxy-8-(2-ethoxy-1,2-dihydroxy-ethyl)-4H-benzo[1,4]oxazin-3-one and 287 mg (1 mmol) 3-(4-amino-4-methyl-pentyl)-3H-benzoxazol-2-one are reacted according to General Method 1. After hydrogenolytic cleaving of the benzyl protective group the crude product is isolated, and from this the product is obtained by stirring in an acetone/diethyl ether mixture.

Yield: 161 mg (29%, trifluoroacetate); mass spectroscopy: [M+H]$^+$=442.

Salt precursor 4: 8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one

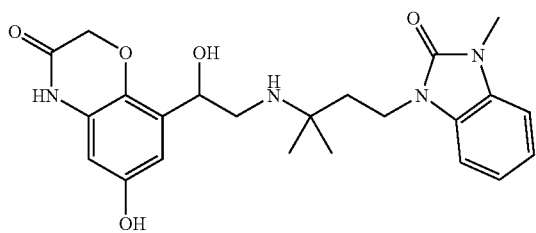

Prepared according to General Method 2 from 357 mg (1 mmol) 6-benzyloxy-8-(2-ethoxy-1,2-dihydroxy-ethyl)-4H-benzo[1,4]oxazin-3-one and 233 mg (1 mmol) 1-(3-amino-3-methyl-butyl)-3-methyl-1,3-dihydro-benzimidazol-2-one.

Yield: 270 mg (61%); mass spectroscopy: [M+H]$^+$=441.

Salt precursor 5: 8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one

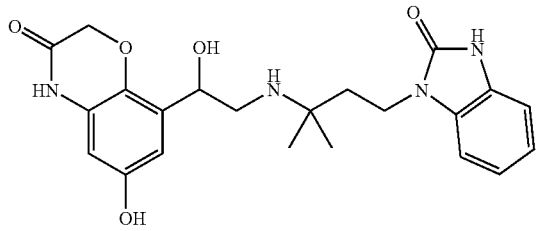

The target compound is prepared according to General Method 2 from 357 mg (1 mmol) 6-benzyloxy-8-(2-ethoxy-1,2-dihydroxy-ethyl)-4H-benzo[1,4]oxazin-3-one and 219 mg (1 mmol) 1-(3-amino-3-methyl-butyl)-1,3-dihydro-benzimidazol-2-one.

Yield: 187 mg (44%); mass spectroscopy: [M+H]$^+$=427.

Salt precursor 5: R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one a) 6-benzyloxy-8-{(R)-2-[1,1-dimethyl-3-(2-oxo-2,3-dihydro-benzimidazol-1-yl)-propylamino]-1-hydroxy-ethyl}-4H-benzo[1,4]oxazin-3-one: 300 mg (1.01 mmol) 6-benzyloxy-8-(R)-oxiranyl-4H-benzo[1,4]oxazin-3-one and 250 mg (1.14 mmol) 1-(3-amino-3-methyl-butyl)-1,3-dihydro-benzimidazol-2-one in 3 mL toluene are stirred for 60 minutes at 160° C. in the microwave (Emrys Optimizer made by Personal Chemistry). After cooling the toluene is decanted off and the residue is chromatographed on a silica gel column. The solid thus obtained (480 mg, 95%) is reacted further without any more purification. Mass spectroscopy: [M+H]$^+$=517.

b) 8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one hydrochloride: 470 mg (95%, 0.86 mmol) 6-benzyloxy-8-{(R)-2-[1,1-dimethyl-3-(2-oxo-2,3-dihydro-benzimidazol-1-yl)-propylamino]-1-hydroxy-ethyl}-4H-benzo[1,4]oxazin-3-one in 40 mL methanol are hydrogenated at ambient temperature and at 3 bar hydrogen pressure with palladium on charcoal as catalyst (10%). Then the catalyst is separated off and the filtrate is evaporated down in vacuo. The residue is dissolved in a little methanol/isopropanol and combined with 5 molar hydrochloric acid in isopropanol. The precipitated solid is filtered off, washed with diethyl ether and dried.

Yield: 335 mg (84%); mass spectroscopy: [M+H]$^+$=427. The free base can be obtained from the hydrochloride by adding dichloromethane to the latter and extracting it with aqueous potassium carbonate solution.

Salt precursor 6: 8-{2-[1,1-dimethyl-4-(2-oxo-2,3-dihydro-benzimidazol-1-yl)-butylamino]-1-hydroxy-ethyl}-6-hydroxy-4H-benzo[1,4]oxazin-3-one

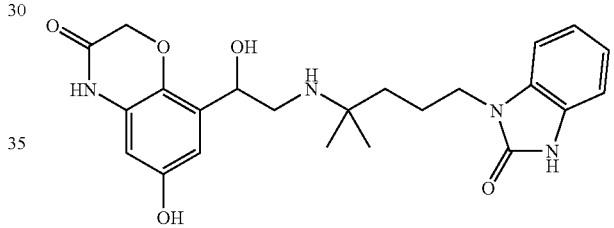

Prepared according to General Method 2 from 357 mg (1 mmol) 6-benzyloxy-8-(2-ethoxy-1,2-dihydroxy-ethyl)-4H-benzo[1,4]oxazin-3-one and 233 mg (1 mmol) 1-(4-amino-4-methyl-pentyl)-1,3-dihydro-benzimidazol-2-one.

Yield: 192 mg (44%); mass spectroscopy: [M+H]$^+$=441.

Salt precursor 7: 8-{2-[1,1-dimethyl-3-(2-oxo-benzoxazol-3-yl)-propylamino]-1-hydroxy-ethyl}-6-hydroxy-4H-benzo[1,4]oxazin-3-one

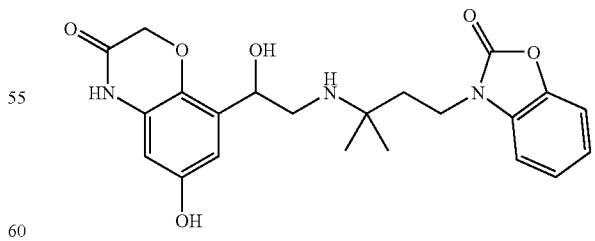

This is prepared according to General Method 1 from 357 mg (1 mmol) 6-benzyloxy-8-(2-ethoxy-1,2-dihydroxy-ethyl)-4H-benzo[1,4]oxazin-3-one and 220 mg (1 mmol) 3-(3-amino-3-methyl-butyl)-3H-benzoxazol-2-one.

Yield: 227 mg (42%, trifluoroacetate); mass spectroscopy: [M+H]$^+$=428.

Salt precursor 8: 6-hydroxy-8-{1-hydroxy-2-[4-(4-methoxy-2-oxo-2,3-dihydro-benzimidazol-1-yl)-1,1-dimethyl-butylamino]-ethyl}-4H-benzo[1,4]oxazin-3-one

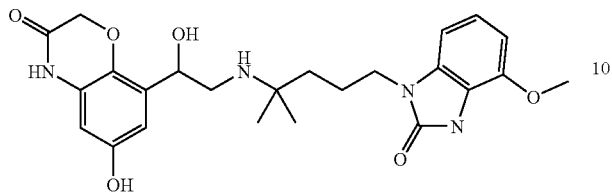

a) 6-benzyloxy-8-{1-hydroxy-2-[4-(4-methoxy-2-oxo-2,3-dihydro-benzimidazol-1-yl)-1,1-dimethyl-butylamino]-ethyl}-4H-benzo[1,4]oxazin-3-on: 200 mg (0.667 mmol) 1-(3-amino-3-methyl-butyl)-4-methoxy-1,3-dihydro-benzimidazol-2-one hydrochloride and 120 μL (0.733 mmol) triethylamine in 5 mL THF are stirred for 30 minutes and then combined with 200 mg (0.666 mmol) 6-benzyloxy-8-(2-ethoxy-2-hydroxy-acetyl)-4H-benzo[1,4]oxazin-3-one. After 2 hours the reaction mixture is cooled to 10° C. and 60 mg (2.76 mmol) lithium borohydride are added. The mixture is stirred for one hour at ambient temperature, then cooled to 10° C. and combined with 15 mL water. The organic phase is extracted with dichloromethane and the combined organic extracts are dried and freed from the solvent. The oil remaining is dissolved in ethyl acetate and adjusted to pH 2 with hydrochloric acid in ethyl acetate. The solvent is distilled off and the residue is stirred with dichloromethane/diethyl ether.

Yield: 130 mg (35%, hydrochloride); mass spectroscopy: [M+H]$^+$=561.

b) 6-hydroxy-8-{1-hydroxy-2-[4-(4-methoxy-2-oxo-2,3-dihydro-benzimidazol-1-yl)-1,1-dimethyl-butylamino]-ethyl}-4H-benzo[1,4]oxazin-3-one: 130 mg (0.213 mmol) 6-benzyloxy-8-{1-hydroxy-2-[4-(4-methoxy-2-oxo-2,3-dihydro-benzimidazol-1-yl)-1,1-dimethyl-butylamino]-ethyl}-4H-benzo[1,4]oxazin-3-one hydrochloride are dissolved in methanol and hydrogenated at normal pressure with palladium on charcoal as catalyst. The catalyst is filtered through Celite, the filtrate is freed from the solvent and the residue is stirred with ethyl acetate. Solid.

Yield: 50 mg (45%, hydrochloride); mass spectroscopy: [M+H]$^+$=471.

Salt precursor 9: 6-hydroxy-8-{1-hydroxy-2-[4-(5-methoxy-3-methyl-2-oxo-2,3-dihydro-benzimidazol-1-yl)-1,1-dimethyl-butylamino]-ethyl}-4H-benzo[1,4]oxazin-3-one

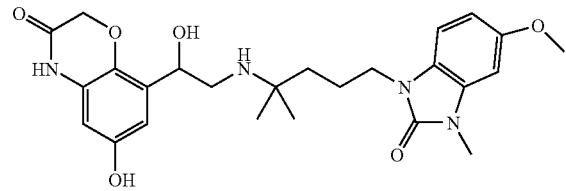

Prepared from 1-(3-amino-3-methyl-butyl)-5-methoxy-3-methyl-1,3-dihydro-benzimidazol-2-one and 6-benzyloxy-8-(2-ethoxy-2-hydroxy-acetyl)-4H-benzo[1,4]oxazin-3-one analogously to the method described for Salt precursor 8. Mass spectroscopy: [M+H]$^+$=485.

Salt precursor 10: 8-{2-[4-(6-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one

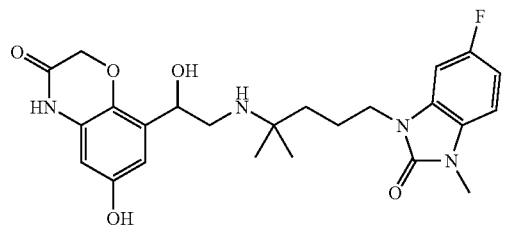

a) 6-benzyloxy-8-{2-[4-(6-fluoro-3-methyl-2-oxo-2,3-dihydro-benzimidazol-1-yl)-1,1-dimethyl-butylamino]-1-hydroxy-ethyl}-4H-benzo[1,4]oxazin-3-one: 200 mg (0.754 mmol) 3-(4-amino-4-methyl-pentyl)-5-fluoro-1-methyl-1,3-dihydro-benzimidazol-2-one hydrochloride and 237 mg (0.663 mmol) 6-benzyloxy-8-(2-ethoxy-2-hydroxy-acetyl)-4H-benzo[1,4]oxazin-3-one are reacted analogously to the procedure laid down for Salt precursor 8a. The final purification is carried out by chromatography on a silica gel column. Yield: 164 mg (44%); mass spectroscopy: [M+H]$^+$=563.

b) 8-{2-[4-(6-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one: 164 mg (0.274 mmol) 6-benzyloxy-8-{2-[4-(6-fluoro-3-methyl-2-oxo-2,3-dihydro-benzimidazol-1-yl)-1,1-dimethyl-butylamino]-1-hydroxy-ethyl}-4H-benzo[1,4]oxazin-3-one are debenzylated analogously to the procedure laid down for Salt precursor 8b. For purification the crude product is stirred with ethyl acetate. Mass spectroscopy: [M+H]$^+$=473.

Salt precursor 11: 8-{2-[4-(7-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one

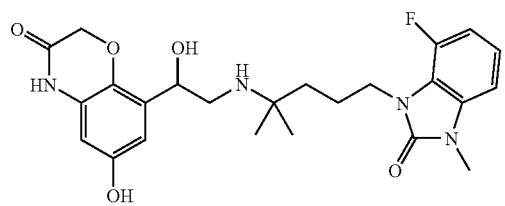

a) 6-benzyloxy-8-{2-[4-(7-fluoro-3-methyl-2-oxo-2,3-dihydro-benzimidazol-1-yl)-1,1-dimethyl-butylamino]-1-hydroxy-ethyl}-4H-benzo[1,4]oxazin-3-one: 200 mg (0.663 mmol) 3-(4-amino-4-methyl-pentyl)-4-fluoro-1-methyl-1,3-dihydro-benzimidazol-2-one hydrochloride and 237 mg (0.663 mmol) 6-benzyloxy-8-(2-ethoxy-2-hydroxy-acetyl)-4H-benzo[1,4]oxazin-3-one are reacted analogously to the procedure laid down for preparing Salt precursor 8a. The final purification of the product is carried out by chromatography on a silica gel column. Yield: 68 mg (17%); mass spectroscopy: [M+H]⁺=563.

b) 8-{2-[4-(7-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one: 68 mg (0.121 mmol) 6-benzyloxy-8-{2-[4-(7-fluoro-3-methyl-2-oxo-2,3-dihydro-benzimidazol-1-yl)-1,1-dimethyl-butylamino]-1-hydroxy-ethyl}-4H-benzo[1,4]oxazin-3-one are debenzylated according to the method described for Salt precursor 8b. For purification the crude product is stirred in ethyl acetate. Yield: 60 mg; mass spectroscopy: [M+H]⁺=474.

Salt precursor 11: R-8-{2-[4-(7-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one a) 6-benzyloxy-8-{(R)-2-[4-(7-fluoro-3-methyl-2-oxo-2,3-dihydro-benzimidazol-1-yl)-1,1-dimethyl-butylamino]-1-hydroxy-ethyl}-4H-benzo[1,4]oxazin-3-one: 595 mg (2.0 mmol) 6-benzyloxy-8-(R)-oxiranyl-4H-benzo[1,4]oxazin-3-one and 743 mg (2.8 mmol) 3-(4-amino-4-methyl-pentyl)-4-fluoro-1-methyl-1,3-dihydro-benzimidazol-2-one in 3.5 mL 2-propanol are stirred at 140° C. in the microwave for 40 minutes. Then the solvent is distilled off in vacuo and the residue is purified on a silica gel column (eluant: dichloromethane/methanol gradient). The corresponding fractions are combined and freed from the solvent. White solid. Yield: 800 mg (71%), mass spectroscopy: [M+H]⁺=563.

b) 8-{(R)-2-[4-(7-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one: 750 mg (1.33 mmol) 6-benzyloxy-8-{(R)-2-[4-(7-fluoro-3-methyl-2-oxo-2,3-dihydro-benzimidazol-1-yl)-1,1-dimethyl-butylamino]-1-hydroxy-ethyl}-4H-benzo[1,4]oxazin-3-one in 15 mL methanol are hydrogenated at ambient temperature and 3 bar hydrogen pressure in the presence of Raney nickel. The catalyst is filtered off and the filtrate is freed from the solvent. White solid. Yield: 550 mg (87%), mass spectroscopy: [M+H]=473.

For syntheses that do not yield an enantiomerically pure product, the R-enantiomer according to the invention may be obtained from the racemate using methods known per se in the prior art.

Synthesis of Salts

The compounds of formula 1 may be prepared according to the following general procedure.

a) Maleate: 1.17 mmol of one of the compounds of the salt precursors 1-11 are dissolved in 5 ml of ethanol at 60° C. After the addition of 0.14 g (1.17 mmol) maleic acid the mixture is cooled to ambient temperature and stirred for 4 hours. The solid formed is filtered off, washed with ethanol and dried for 12 hours at 45° C.

Yield: about 80-90% of theory, the cation to anion stoichiometry is 1:1.

b) L-(+)-tartrate: 35.2 mmol of one of the compounds of the salt precursors 1-11 are dissolved in 150 ml of ethanol at ambient temperature. The solution is heated to 60° C. and a solution of 5.3 g (35.2 mmol) L-(+)-tartaric acid in 40 ml of ethanol is added dropwise. The mixture is cooled to ambient temperature over 6 hours and the resulting solid is filtered. The isolated solid is washed with 40 ml of ethanol and dried for 12 hours at 45° C.

Yield: about 65-75% of theory, the cation to anion stoichiometry is 1:1.

c) Hemi-ethanedisulphonate: 3.52 mmol of one of the compounds of the salt precursors 1-11 are dissolved in 15 ml boiling ethanol and mixed with 0.67 g (3.52 mmol) ethanedisulphonic acid. The mixture is refluxed for 1 hour and then cooled to ambient temperature. After 12 hours at ambient temperature the solid formed is filtered off, washed with 10 ml of ethanol and dried for 12 hours at 45° C.

Yield: about 40-50% of theory, the cation to anion stoichiometry is 2:1.

The compounds named below may be prepared according to the above-mentioned processes a-c:

Example 1

R-8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one maleate Example 2

R-8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one maleate Example 3

R-8-{2-[1,1-dimethyl-4-(2-oxo-benzoxazol-3-yl)-butylamino]-1-hydroxy-ethyl}-6-hydroxy-4H-benzo[1,4]oxazin-3-one maleate Example 4

R-8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one maleate Example 5

R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one maleate Example 6

R-8-{2-[1,1-dimethyl-4-(2-oxo-2,3-dihydro-benzimidazol-1-yl)-butylamino]-1-hydroxy-ethyl}-6-hydroxy-4H-benzo[1,4]oxazin-3-one maleate Example 7

R-8-{2-[1,1-dimethyl-3-(2-oxo-benzoxazol-3-yl)-propylamino]-1-hydroxy-ethyl}-6-hydroxy-4H-benzo[1,4]oxazin-3-one maleate Example 8

R-6-hydroxy-8-{1-hydroxy-2-[4-(4-methoxy-2-oxo-2,3-dihydro-benzimidazol-1-yl)-1,1-dimethyl-butylamino]-ethyl}-4H-benzo[1,4]oxazin-3-one maleate

Example 9

R-6-hydroxy-8-{1-hydroxy-2-[4-(5-methoxy-3-methyl-2-oxo-2,3-dihydro-benzimidazol-1-yl)-1,1-dimethyl-butylamino]-ethyl}-4H-benzo[1,4]oxazin-3-one maleate

Example 10

R-8-{2-[4-(6-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one maleate

Example 11

R-8-{2-[4-(7-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one maleate

Example 12

R-8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one tartrate

Example 13

R-8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one tartrate

Example 14

R-8-{2-[1,1-dimethyl-4-(2-oxo-benzoxazol-3-yl)-butylamino]-1-hydroxy-ethyl}-6-hydroxy-4H-benzo[1,4]oxazin-3-one tartrate

Example 15

R-8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one tartrate

Example 16

R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one tartrate

Example 17

R-8-{2-[1,1-dimethyl-4-(2-oxo-2,3-dihydro-benzimidazol-1-yl)-butylamino]-1-hydroxy-ethyl}-6-hydroxy-4H-benzo[1,4]oxazin-3-one tartrate

Example 18

R-8-{2-[1,1-dimethyl-3-(2-oxo-benzoxazol-3-yl)-propylamino]-1-hydroxy-ethyl}-6-hydroxy-4H-benzo[1,4]oxazin-3-one tartrate

Example 19

R-6-hydroxy-8-{1-hydroxy-2-[4-(4-methoxy-2-oxo-2,3-dihydro-benzimidazol-1-yl)-1,1-dimethyl-butylamino]-ethyl}-4H-benzo[1,4]oxazin-3-one tartrate

Example 20

R-6-hydroxy-8-{1-hydroxy-2-[4-(5-methoxy-3-methyl-2-oxo-2,3-dihydro-benzimidazol-1-yl)-1,1-dimethyl-butylamino]-ethyl}-4H-benzo[1,4]oxazin-3-one tartrate

Example 21

R-8-{2-[4-(6-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one tartrate

Example 22

R-8-{2-[4-(7-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one tartrate

Example 23

R-8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one hemi-ethanedisulphonate

Example 24

R-8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one hemi-ethanedisulphonate

Example 25

R-8-{2-[1,1-dimethyl-4-(2-oxo-benzoxazol-3-yl)-butylamino]-1-hydroxy-ethyl}-6-hydroxy-4H-benzo[1,4]oxazin-3-one hemi-ethanedisulphonate

Example 26

R-8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one hemi-ethanedisulphonate

Example 27

R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one hemi-ethanedisulphonate

Example 28

R-8-{2-[1,1-dimethyl-4-(2-oxo-2,3-dihydro-benzimidazol-1-yl)-butylamino]-1-hydroxy-ethyl}-6-hydroxy-4H-benzo[1,4]oxazin-3-one hemi-ethanedisulphonate

Example 29

R-8-{2-[1,1-dimethyl-3-(2-oxo-benzoxazol-3-yl)-propylamino]-1-hydroxy-ethyl}-6-hydroxy-4H-benzo[1,4]oxazin-3-one hemi-ethanedisulphonate

Example 30

R-6-hydroxy-8-{1-hydroxy-2-[4-(4-methoxy-2-oxo-2,3-dihydro-benzimidazol-1-yl)-1,1-dimethyl-butylamino]-ethyl}-4H-benzo[1,4]oxazin-3-one hemi-ethanedisulphonate

Example 31

R-6-hydroxy-8-{1-hydroxy-2-[4-(5-methoxy-3-methyl-2-oxo-2,3-dihydro-benzimidazol-1-yl)-1,1-dimethyl-butylamino]-ethyl}-4H-benzo[1,4]oxazin-3-one hemi-ethanedisulphonate

Example 32

R-8-{2-[4-(6-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one hemi-ethanedisulphonate

Example 33

R-8-{2-[4-(7-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one hemi-ethanedisulphonate X-Ray Powder Diagram Relating to Example 5

Parameters of the X-ray powder diffractometer used for the measurement: STOE Stadi P X-ray powder diffractometer with a location-sensitive detector in transmission mode with a curved germanium (111) primary monochromator; wavelength used: $CuK_{\alpha 1}$ with $\lambda=1.540598$ Å; power capacity of the X-ray tube: 40 kV, 40 mA; recording range: 3-40° 2Θ.

The following Table shows the characteristic X-ray reflections with intensities (standardised, up to 40° 2Θ) for the Example specified. As the skilled man knows, the intensities of the reflections may vary depending on the preparation of the samples. The intensities given below were recorded in one measurement of the Example specified above and cannot be applied to every other measurement.

| 2Θ [°] | $d_{hkl}$ [Å] | intensity $I/I_o$ [%] |
|---|---|---|
| 3.83 | 23.02 | 100 |
| 9.73 | 9.09 | 44 |
| 10.26 | 8.62 | 6 |
| 11.19 | 7.90 | 10 |
| 11.57 | 7.64 | 23 |
| 12.26 | 7.21 | 83 |
| 14.60 | 6.06 | 48 |
| 14.98 | 5.91 | 38 |
| 15.48 | 5.72 | 11 |
| 16.47 | 5.38 | 5 |
| 17.45 | 5.08 | 70 |
| 17.79 | 4.98 | 19 |
| 18.20 | 4.87 | 56 |
| 19.14 | 4.63 | 29 |
| 19.88 | 4.46 | 84 |
| 21.46 | 4.14 | 6 |
| 22.70 | 3.91 | 53 |
| 23.33 | 3.81 | 56 |
| 24.22 | 3.67 | 76 |
| 25.29 | 3.52 | 6 |
| 26.09 | 3.41 | 18 |
| 26.76 | 3.33 | 9 |
| 27.50 | 3.24 | 56 |
| 28.84 | 3.09 | 14 |
| 29.17 | 3.06 | 22 |
| 30.81 | 2.90 | 11 |
| 31.33 | 2.85 | 8 |
| 31.81 | 2.81 | 4 |
| 32.42 | 2.76 | 7 |
| 32.76 | 2.73 | 6 |
| 33.74 | 2.65 | 4 |
| 34.58 | 2.59 | 14 |
| 35.17 | 2.55 | 11 |
| 35.54 | 2.52 | 6 |
| 35.94 | 2.50 | 4 |
| 36.52 | 2.46 | 3 |
| 37.65 | 2.39 | 4 |
| 38.79 | 2.32 | 6 |
| 39.54 | 2.28 | 8 |

Thermoanalysis (DSC/TG) Relating to Example 5

Technical data relating to the thermoanalytical DSC device used: DSC 822 made by Mettler Toledo; heating rate: 10 K/min; type of crucible: perforated aluminium crucible; atmosphere: $N_2$, 80 ml/min flux; weight: 12.4 mg.

Technical data relating to the thermoanalytical TG device used: TGA/SDTA 851 made by Mettler Toledo with IR coupling (Nicolet FT-IR 4700) for analysing the volatile fractions driven off; heating rate: 10 K/min; type of crucible: open aluminium oxide crucible; atmosphere: $N_2$, 20 ml/min flux; weight: 27.8 mg.

The above Example for which the X-ray powder diffractogram was also produced has an endothermic maximum at about 237° C. with decomposition (FIG. 1).

X-Ray Powder Diagram Relating to Example 16

Parameters of the X-ray powder diffractometer used for the measurement: STOE Stadi P X-ray powder diffractometer with a location-sensitive detector in transmission mode with a curved germanium (111) primary monochromator; wavelength used: $CuK_{\alpha 1}$ with $\lambda=1.540598$ Å; power capacity of the X-ray tube: 40 kV, 40 mA; recording range: 3-40° 2Θ.

The following Table shows the characteristic X-ray reflections with intensities (standardised, up to 40° 2Θ) for the Example specified. As the skilled man knows, the intensities of the reflections may vary depending on the preparation of the samples. The intensities given below were recorded in one measurement of the Example specified above and cannot be applied to every other measurement.

| 2Θ [°] | $d_{hkl}$ [Å] | intensity $I/I_o$ [%] |
|---|---|---|
| 3.97 | 22.23 | 100 |
| 10.44 | 8.47 | 18 |
| 11.24 | 7.86 | 15 |
| 11.94 | 7.41 | 17 |
| 13.22 | 6.69 | 27 |
| 14.87 | 5.95 | 6 |
| 15.73 | 5.63 | 95 |
| 15.96 | 5.55 | 14 |
| 16.35 | 5.42 | 22 |
| 16.88 | 5.25 | 46 |
| 17.36 | 5.11 | 31 |

| 2Θ [°] | $d_{hkl}$ [Å] | intensity $I/I_o$ [%] |
|---|---|---|
| 18.30 | 4.84 | 63 |
| 19.27 | 4.60 | 3 |
| 19.96 | 4.44 | 7 |
| 20.34 | 4.36 | 34 |
| 20.95 | 4.24 | 19 |
| 21.26 | 4.18 | 32 |
| 21.42 | 4.14 | 14 |
| 22.37 | 3.97 | 7 |
| 22.61 | 3.93 | 12 |
| 22.76 | 3.90 | 18 |
| 23.05 | 3.86 | 67 |
| 23.64 | 3.76 | 19 |
| 24.00 | 3.71 | 8 |
| 24.40 | 3.65 | 10 |
| 24.77 | 3.59 | 13 |
| 25.25 | 3.52 | 18 |
| 25.58 | 3.48 | 49 |
| 25.76 | 3.46 | 19 |
| 26.07 | 3.41 | 6 |
| 26.49 | 3.36 | 29 |
| 27.16 | 3.28 | 15 |
| 27.41 | 3.25 | 8 |
| 27.67 | 3.22 | 22 |
| 28.01 | 3.18 | 8 |
| 28.52 | 3.13 | 4 |
| 29.03 | 3.07 | 4 |
| 29.36 | 3.04 | 8 |
| 29.88 | 2.99 | 10 |
| 30.21 | 2.96 | 5 |
| 30.85 | 2.90 | 3 |
| 31.76 | 2.81 | 5 |
| 31.96 | 2.80 | 8 |
| 32.45 | 2.76 | 10 |
| 32.85 | 2.72 | 11 |
| 33.73 | 2.66 | 7 |
| 34.23 | 2.62 | 10 |
| 34.99 | 2.56 | 9 |
| 35.63 | 2.52 | 3 |
| 36.54 | 2.46 | 5 |
| 37.05 | 2.42 | 4 |
| 37.28 | 2.41 | 4 |
| 37.71 | 2.38 | 3 |
| 38.49 | 2.34 | 8 |

Thermoanalysis (DSC/TG) Relating to Example 16

Technical data relating to the thermoanalytical DSC device used: DSC 822 made by Mettler Toledo; heating rate: 10 K/min; type of crucible: perforated aluminium crucible; atmosphere: $N_2$, 80 ml/min flux; weight: 12.4 mg.

Technical data relating to the thermoanalytical TG device used: TGA/SDTA 851 made by Mettler Toledo with IR coupling (Nicolet FT-IR 4700) for analysing the volatile fractions driven off; heating rate: 10 K/min; type of crucible: open aluminium oxide crucible; atmosphere: $N_2$, 20 ml/min flux; weight: 27.8 mg.

Figure 2:
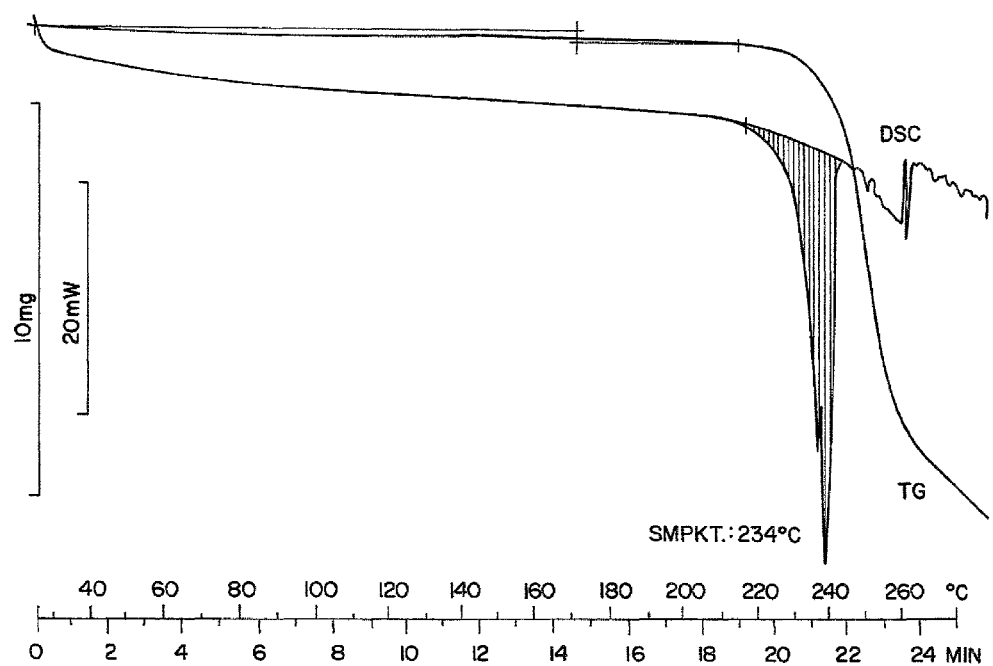
FIG. 2: Differential scanning calorimetry plot of Example 16.

The above Example for which the X-ray powder diffractogram was also produced has an endothermic maximum at about 234° C. with decomposition (FIG. 2).

X-Ray Powder Diagram Relating to Example 27

Parameters of the X-ray powder diffractometer used for the measurement: STOE Stadi P X-ray powder diffractometer with a location-sensitive detector in transmission mode with a curved germanium (111) primary monochromator; wavelength used: $CuK_{\alpha 1}$ with λ=1.540598 Å; power capacity of the X-ray tube: 40 kV, 40 mA; recording range: 3-40° 2Θ.

The following Table shows the characteristic X-ray reflections with intensities (standardised, up to 40° 2Θ) for the Example specified. As the skilled man knows, the intensities of the reflections may vary depending on the preparation of the samples. The intensities given below were recorded in one measurement of the Example specified above and cannot be applied to every other measurement.

| 2Θ [°] | $d_{hkl}$ [Å] | intensity $I/I_o$ [%] |
|---|---|---|
| 7.25 | 12.18 | 90 |
| 8.22 | 10.75 | 88 |
| 8.90 | 9.92 | 24 |
| 9.46 | 9.34 | 48 |
| 11.36 | 7.78 | 14 |
| 12.76 | 6.93 | 67 |
| 13.20 | 6.70 | 14 |
| 14.52 | 6.09 | 52 |
| 14.82 | 5.97 | 25 |
| 15.58 | 5.68 | 40 |
| 16.51 | 5.36 | 46 |
| 16.82 | 5.27 | 28 |
| 17.20 | 5.15 | 15 |
| 18.08 | 4.90 | 21 |
| 18.89 | 4.69 | 79 |
| 20.02 | 4.43 | 77 |
| 20.25 | 4.38 | 35 |
| 20.88 | 4.25 | 24 |
| 21.18 | 4.19 | 37 |
| 21.87 | 4.06 | 24 |
| 22.16 | 4.01 | 16 |
| 22.66 | 3.92 | 11 |
| 23.16 | 3.84 | 37 |
| 23.70 | 3.75 | 100 |
| 24.48 | 3.63 | 24 |
| 25.82 | 3.45 | 65 |
| 26.07 | 3.42 | 25 |
| 26.59 | 3.35 | 10 |
| 26.94 | 3.31 | 8 |
| 27.65 | 3.22 | 8 |
| 28.77 | 3.10 | 15 |
| 29.61 | 3.01 | 19 |
| 29.89 | 2.99 | 24 |
| 32.69 | 2.74 | 14 |
| 33.90 | 2.64 | 8 |
| 34.79 | 2.58 | 11 |
| 36.58 | 2.45 | 8 |
| 36.84 | 2.44 | 12 |
| 30.21 | 2.96 | 5 |
| 30.85 | 2.90 | 3 |
| 31.76 | 2.81 | 5 |
| 31.96 | 2.80 | 8 |
| 32.45 | 2.76 | 10 |
| 32.85 | 2.72 | 11 |
| 33.73 | 2.66 | 7 |
| 34.23 | 2.62 | 10 |
| 34.99 | 2.56 | 9 |
| 35.63 | 2.52 | 3 |
| 36.54 | 2.46 | 5 |
| 37.05 | 2.42 | 4 |
| 37.28 | 2.41 | 4 |
| 37.71 | 2.38 | 3 |
| 38.49 | 2.34 | 8 |
| 39.13 | 2.30 | 6 |

Thermoanalysis (DSC/TG) Relating to Example 27

Technical data relating to the thermoanalytical DSC device used: DSC 822 made by Mettler Toledo; heating rate: 10 K/min; type of crucible: perforated aluminium crucible; atmosphere: $N_2$, 80 ml/min flux; weight: 12.4 mg.

Technical data relating to the thermoanalytical TG device used: TGA/SDTA 851 made by Mettler Toledo with IR coupling (Nicolet FT-IR 4700) for analysing the volatile fractions driven off; heating rate: 10 K/min; type of crucible: open aluminium oxide crucible; atmosphere: $N_2$, 20 ml/min flux; weight: 27.8 mg.

Figure 3:
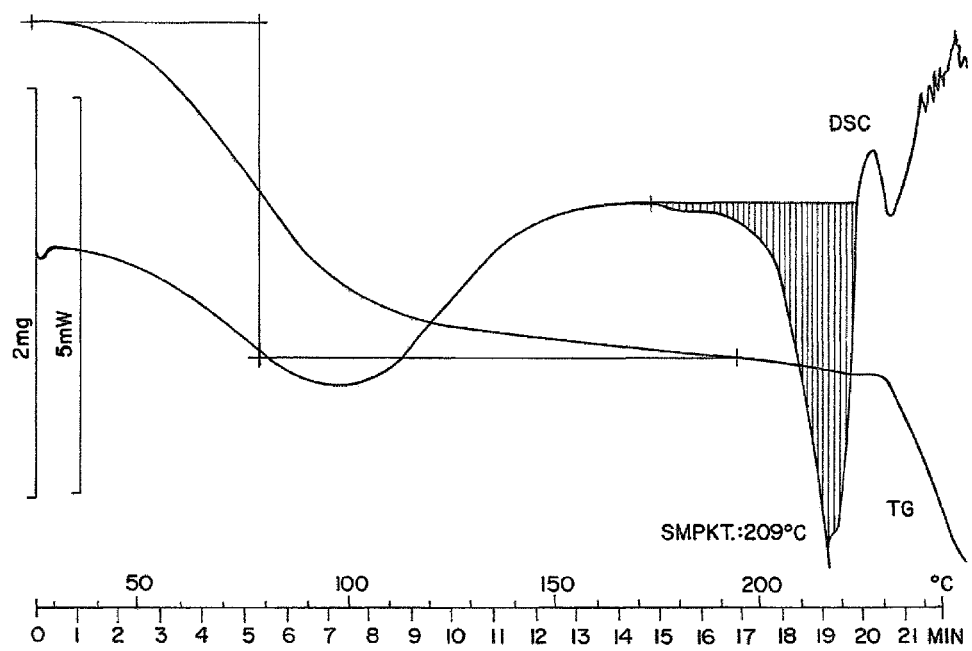
FIG. 3: Differential scanning calorimetry plot of Example 27.

The above Example for which the X-ray powder diffractogram was also produced has an endothermic maximum at about 209° C. with decomposition and is in the form of the hydrate (FIG. 3).

Combinations

The compounds of formula 1 may be used on their own or in combination with other active substances of formula 1. If desired the compounds of formula 1 may also be used in combination with W, where W denotes a pharmacologically active substance and (for example) is selected from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined with the compounds of formula 1. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5,6-diethyl-indan-2-ylamino)-1-hydroxy-ethyl]-8-hydroxy-1H-quinoline-2-one 4-hydroxy-7-[2-{[2-{[3-(2-phenylethoxy)propyl] sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino] ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazole-3-yl]-2-methyl-2-butylamino}ethanol 5-hydroxy-8-(1-hydroxy-2-isopropylaminobutyl)-2H-1,4-benzoxazin-3-(4H)-on 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-1,1-dimethyl-ethylamino]-ethyl}-4H-benzo[1,4]oxazin-3-one 6-hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-dimethyl-2-(2,4,6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1.1dimethyl-ethylamino]-ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3,4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tert-butylamino)ethanol optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

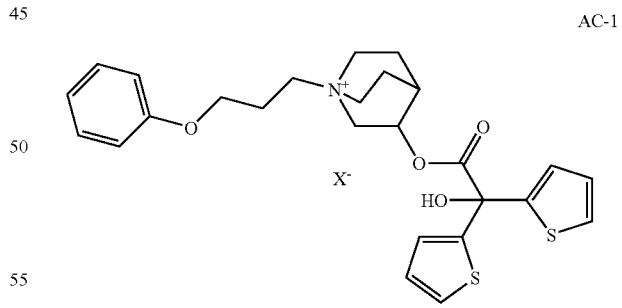

AC-1 wherein $X^-$ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-ene AC-1-ene

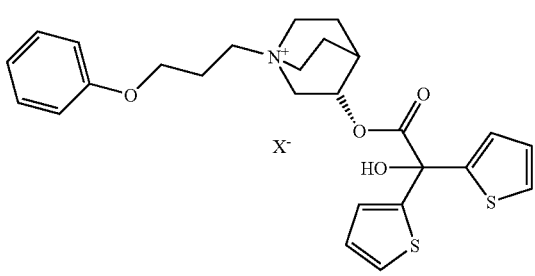

wherein X⁻ may have the above-mentioned meanings. Other preferred anticholinergics are selected from the salts of formula AC-2

AC-2

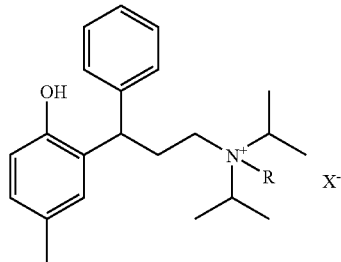

wherein R denotes either methyl or ethyl and wherein X⁻ may have the above-mentioned meanings. In an alternativen embodiment the compound of formula AC-2 may also be present in the form of the free base AC-2-base.

AC-2-base

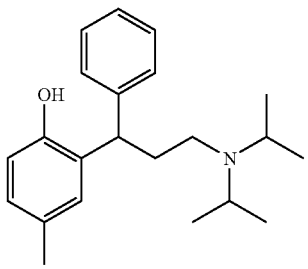

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate-methobromide;
scopine 9-methyl-xanthene-9-carboxylate-methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the salts metho-X are used, wherein X may have the meanings given hereinbefore for X⁻.

As corticosteroids it is preferable to use compounds selected from among prednisolone, prednisone, butixocort propionate, flunisolide, beclomethasone, triamcinolone, budesonide, fluticasone, mometasone, ciclesonide, rofleponide, dexamethasone, betamethasone, deflazacort, RPR-106541, NS-126, ST-26 and (S)-fluoromethyl 6,9-difluoro-17-[(2-furanylcarbonyl)oxy]-11-hydroxy-16-methyl-3-oxo-androsta-1,4-diene-17-carbothionate (S)-(2-oxo-tetrahydro-furan-3S-yl)6,9-difluoro-11-hydroxy-16-methyl-3-oxo-17-propionyloxy-androsta-1,4-diene-17-carbothionate, etiprednol-dichloroacetate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, C1-1018, CDC-801, CDC-3052, D-22888, YM-58997, Z-15370 and N-(3,5-dichloro-1-oxo-pyridin-4-yl)-4-difluoromethoxy-3-cyclopropylmethoxybenzamide (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide (R)-(+)-1-(4-bromobenzyl)-4-[(3-cyclopentyloxy)-4-methoxyphenyl]-2-pyrrolidone 3-(cyclopentyloxy-4-methoxyphenyl)-1-(4-N'-[N-2-cyano-S-methyl-isothioureido]benzyl)-2-pyrrolidone cis[4-cyano-4-(3-cyclopentyloxy-4-methoxyphenyl)cyclohexane-1-carboxylic acid]

2-carbomethoxy-4-cyano-4-(3-cyclopropylmethoxy-4-difluoromethoxy-phenyl)cyclohexan-1-one cis[4-cyano-4-(3-cyclopropylmethoxy-4-difluoromethoxyphenyl)cyclohexan-1-ol]

(R)-(+)-ethyl[4-(3-cyclopentyloxy-4-methoxyphenyl)pyrrolidin-2-ylidene]acetate (S)-(−)-ethyl[4-(3-cyclopentyloxy-4-methoxyphenyl)pyrrolidin-2-ylidene]acetate 9-cyclopentyl-5,6-dihydro-7-ethyl-3-(2-thienyl)-9H-pyrazolo[3,4-c]-1,2,4-triazolo[4,3-a]pyridine 9-cyclopentyl-5,6-dihydro-7-ethyl-3-(tert-butyl)-9H-pyrazolo[3,4-c]-1,2,4-triazolo[4,3-a]pyridine optionally in the form of the racemates, enantiomers or diastereomers thereof and optionally in the form of the pharmacologically acceptable acid addition salts thereof, the solvates and/or hydrates thereof According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-3-(2-(6,7-difluoro-2-quinolinyl)ethenyl)phenyl)-3-(2-(2-hydroxy-2-propyl)phenyl)thio)methylcyclopropane-acetic acid, 1-(((1R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]-amino}-7-cyclopropylmethoxy-quinazoline 4-[(3-chloro-4-fluorophenyl)amino]-6-{[4-(N,N-diethylamino)-1-oxo-2-buten-1-yl]-amino}-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopropylmethoxy-quinazoline 4-[(R)-(1-phenyl-ethyl)amino]-6-{[4-(morpholin-4-yl)-1-oxo-2-buten-1-yl]amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6,7-bis-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5,5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yl-oxy}-7-methoxy-quinazoline 4-[(3-chloro-4-fluoro-phenyl)amino]-6-{1-[(methoxymethyl)carbonyl]-piperidin-4-yl-oxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethansulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7(2-methoxy-ethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methylamino-cyclohexan-1-yloxy)-7-methoxy-quinazoline 4-[(3-chloro-4-fluoro-phenyl)amino]-6-{cis-4-[N-(2-methoxy-acetyl)-N-methyl-amino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1-[(2-methyl-morpholin-4-yl)carbonyl]-piperidin-4-yloxy}-7-methoxy-quinazoline 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline 4-[(3-chloro-4-fluoro-phenyl)amino]-6-{1-[(N-methyl-N-2-methoxyethyl-amino)carbonyl]-piperidin-4-yloxy}-7-methoxy-quinazoline 4-[(3-chloro-4-fluoro-phenyl)amino]-6-(1-ethyl-piperidin-4-yloxy)-7-methoxy-quinazoline 4-[(3-chloro-4-fluoro-phenyl)amino]-6-{1-[(2-methoxyethyl)carbonyl]-piperidin-4-yloxy}-7-methoxy-quinazoline 4-[(3-chloro-4-fluoro-phenyl)amino]-6-{1-[(3-methoxypropyl-amino)-carbonyl]-piperidin-4-yloxy}-7-methoxy-quinazoline 4-[(3-chloro-4-fluoro-phenyl)amino]-6-[cis-4-(N-methanesulphonyl-N-methyl-amino)-cyclohexan-1-yloxy]-7-methoxy-quinazoline 4-[(3-chloro-4-fluoro-phenyl)amino]-6-[cis-4-(N-acetyl-N-methyl-amino)-cyclohexan-1-yloxy]-7-methoxy-quinazoline 4-[(3-chloro-4-fluoro-phenyl)amino]-6-(trans-4-methylamino-cyclohexan-1-yloxy)-7-methoxy-quinazoline 4-[(3-chloro-4-fluoro-phenyl)amino]-6-[trans-4-(N-methanesulphonyl-N-methyl-amino)-cyclohexan-1-yloxy]-7-methoxy-quinazoline 4-[(3-chloro-4-fluoro-phenyl)amino]-6-(trans-4-dimethylamino-cyclohexan-1-yloxy)-7-methoxy-quinazoline 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorphenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The PAF-antagonists used are preferably compounds selected from among 4-(2-chlorophenyl)-9-methyl-2-[3(4-morpholinyl)-3-propanon-1-yl]-6H-thieno-[3,2-f]-[1,2,4]triazolo[4,3-a][1,4]diazepine 6-(2-chlorophenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4]diazepine, optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Formulations

Suitable pharmaceutical compositions and formulation for administering the compounds of formula 1 include for example tablets, capsules, suppositories, solutions, powders etc. The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilisers such as alkali metal salts of ethylenediaminetetraacetic acid, optionally using emulsifiers and/or dispersants, while if water is used as diluent, for example, organic solvents may optionally be used as solubilisers or dissolving aids, and the solutions may be transferred into injection vials or ampoules or infusion bottles.

Capsules containing the compounds of formula 1 according to the invention may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, preferably potato starch, gelatine and the like. Lubricants such as magnesium stearate, sodium laurylsulphate and talc may also be used to produce the tablets. In the case of aqueous suspensions the active substances may be combined with various flavour enhancers or colourings in addition to the abovementioned excipients.

Use of the compounds of formula 1 for the treatment of respiratory complaints can be administered by inhalation. Inhalable preparations include inhalable powders, propellant-containing metered-dose aerosols or propellant-free inhalable solutions. Within the scope of the present invention, the term propellant-free inhalable solutions also includes concentrates or sterile ready-to-use inhalable solutions.

The compounds of formula 1 may be used in crystalline form according to the invention and used to prepare powders for inhalation. The inhalable powders which may be used according to the invention may contain the crystalline compounds of formula 1 either on their own or in admixture with suitable physiologically acceptable excipients.

If the active ingredients are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 μm, preferably between 10 and 150 μm, most preferably between 15 and 80 μm. In some cases it may seem appropriate to add finer excipient fractions with an average particle size of 1 to 9 μm to the excipients mentioned above. These finer excipients are also selected from the group of possible excipients listed hereinbefore. Finally, in order to prepare the inhalable powders according to the invention, micronised active substance, preferably with an average particle size of 0.5 to 10 μm, more preferably from 1 to 5 μm, is added to the excipient mixture. Processes for producing the inhalable powders according to the invention by grinding and micronising and finally mixing the ingredients together are known from the prior art.

The inhalable powders according to the invention may be administered using inhalers known from the prior art.

The inhalation aerosols containing propellant gas according to the invention may contain dissolved in the propellant gas or in dispersed form. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The above-mentioned propellant gases may be used on their own or in admixture. Particularly preferred propellant gases are halogenated alkane derivatives selected from TG134a and TG227 and mixtures thereof.

The propellant-driven inhalation aerosols may also contain other ingredients such as co-solvents, stabilisers, surfactants, antioxidants, lubricants and pH adjusters. All these ingredients are known in the art.

The propellant-driven inhalation aerosols mentioned above may be administered using inhalers known in the art (MDIs=metered dose inhalers).

The dosage of the compounds according to the invention is naturally highly dependent on the method of administration and the complaint which is being treated. When administered by inhalation the compounds of the formula are characterised by a high potency even at doses in the μg range. The compounds of the formula may also be used effectively above the μg range. The dosage may then be in the milligram range, for example.

In another aspect the present invention relates to the above-mentioned pharmaceutical formulations (compositions) as such, which are characterised in that they contain a compound of formula 1, in the above-mentioned pharmaceutical formulations administered by inhalation.

The following examples of formulations illustrate the present invention without restricting its scope:

Examples of Pharmaceutical Formulations

| A) Tablets | per tablet |
|---|---|
| active substance | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance | 80 mg |
| corn starch | 190 mg |
| lactose | 55 mg |
| microcrystalline cellulose | 35 mg |

| B) Tablets | per tablet |
| --- | --- |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C) Coated tablets | per coated tablet |
| --- | --- |
| Active substance | 5 mg |
| Corn starch | 41.5 mg |
| Lactose | 30 mg |
| Polyvinylpyrrolidone | 3 mg |
| Magnesium stearate | 0.5 mg |
| | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| D) Capsules | per capsule |
| --- | --- |
| Active substance | 50 mg |
| Corn starch | 268.5 mg |
| Magnesium stearate | 1.5 mg |
| | 320 mg |

The substance and corn starch are mixed and moistened with water. The moist mass is screened and dried. The dry granules are screened and mixed with magnesium stearate. The finished mixture is packed into size 1 hard gelatine capsules.

| E) Ampoule solution | |
| --- | --- |
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| F) Suppositories | |
| --- | --- |
| Active substance | 50 mg |
| Solid fat | 1650 mg |
| | 1700 mg |

The hard fat is melted. At 40° C. the ground active substance is homogeneously dispersed therein. It is cooled to 38° C. and poured into slightly chilled suppository moulds.

| G) Oral suspension | |
| --- | --- |
| active substance | 50 mg |
| hydroxyethylcellulose | 50 mg |
| sorbic acid | 5 mg |
| sorbitol (70%) | 600 mg |
| glycerol | 200 mg |
| flavouring | 15 mg |
| water ad | 5 ml |

Distilled water is heated to 70° C. Hydroxyethyl-cellulose is dissolved therein with stirring. After the addition of sorbitol solution and glycerol the preparation is cooled to ambient temperature. At ambient temperature the sorbic acid, flavouring and substance are added. The suspension is evacuated with stirring to eliminate any air.

We claim:

1. A compound selected from the group consisting of:
R-8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one maleate,
R-8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one maleate,
R-8-{2-[1,1-dimethyl-4-(2-oxo-benzoxazol-3-yl)-butylamino]-1-hydroxy-ethyl}-6-hydroxy-4H-benzo[1,4]oxazin-3-one maleate,
R-8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one maleate,
R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one maleate,
R-8-{2-[1,1-dimethyl-4-(2-oxo-2,3-dihydro-benzimidazol-1-yl)-butylamino]-1-hydroxy-ethyl}-6-hydroxy-4H-benzo[1,4]oxazin-3-one maleate,
R-8-{2-[1,1-dimethyl-3-(2-oxo-benzoxazol-3-yl)-propylamino]-1-hydroxy-ethyl}-6-hydroxy-4H-benzo[1,4]oxazin-3-one maleate,
R-6-hydroxy-8-{1-hydroxy-2-[4-(4-methoxy-2-oxo-2,3-dihydro-benzimidazol-1-yl)-1,1-dimethyl-butylamino]-ethyl}-4H-benzo[1,4]oxazin-3-one maleate,
R-6-hydroxy-8-{1-hydroxy-2-[4-(5-methoxy-3-methyl-2-oxo-2,3-dihydro-benzimidazol-1-yl)-1,1-dimethyl-butylamino]-ethyl}-4H-benzo[1,4]oxazin-3-one maleate,
R-8-{2-[4-(6-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one maleate,
R-8-{2-[4-(7-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one maleate, R-8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one tartrate,
R-8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one tartrate,
R-8-{2-[1,1-dimethyl-4-(2-oxo-benzoxazol-3-yl)-butylamino]-1-hydroxy-ethyl}-6-hydroxy-4H-benzo[1,4]oxazin-3-one tartrate,
R-8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one tartrate,
R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one tartrate,
R-8-{2-[1,1-dimethyl-4-(2-oxo-2,3-dihydro-benzimidazol-1-yl)-butylamino]-1-hydroxy-ethyl}-6-hydroxy-4H-benzo[1,4]oxazin-3-one tartrate,
R-8-{2-[1,1-dimethyl-3-(2-oxo-benzoxazol-3-yl)-propylamino]-1-hydroxy-ethyl}-6-hydroxy-4H-benzo[1,4]oxazin-3-one tartrate,
R-6-hydroxy-8-{1-hydroxy-2-[4-(4-methoxy-2-oxo-2,3-dihydro-benzimidazol-1-yl)-1,1-dimethyl-butylamino]-ethyl}-4H-benzo[1,4]oxazin-3-one tartrate,
R-6-hydroxy-8-{1-hydroxy-2-[4-(5-methoxy-3-methyl-2-oxo-2,3-dihydro-benzimidazol-1-yl)-1,1-dimethyl-butylamino]-ethyl}-4H-benzo[1,4]oxazin-3-one tartrate,
R-8-{2-[4-(6-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one tartrate,
R-8-{2-[4-(7-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one tartrate,
R-8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one hemi-ethanedisulphonate,
R-8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one hemi-ethanedisulphonate,
R-8-{2-[1,1-dimethyl-4-(2-oxo-benzoxazol-3-yl)-butylamino]-1-hydroxy-ethyl}-6-hydroxy-4H-benzo[1,4]oxazin-3-one hemi-ethanedisulphonate,
R-8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one hemi-ethanedisulphonate,
R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one hemi-ethanedisulphonate,
R-8-{2-[1,1-dimethyl-4-(2-oxo-2,3-dihydro-benzimidazol-1-yl)-butylamino]-1-hydroxy-ethyl}-6-hydroxy-4H-benzo[1,4]oxazin-3-one hemi-ethanedisulphonate,
R-8-{2-[1,1-dimethyl-3-(2-oxo-benzoxazol-3-yl)-propylamino]-1-hydroxy-ethyl}-6-hydroxy-4H-benzo[1,4]oxazin-3-one hemi-ethanedisulphonate,
R-6-hydroxy-8-{1-hydroxy-2-[4-(4-methoxy-2-oxo-2,3-dihydro-benzimidazol-1-yl)-1,1-dimethyl-butylamino]-ethyl}-4H-benzol-[1,4]oxazin-3-one hemi-ethanedisulphonate,
R-6-hydroxy-8-{1-hydroxy-2-[4-(5-methoxy-3-methyl-2-oxo-2,3-dihydro-benzimidazol-1-yl)-1,1-dimethyl-butylamino]-ethyl}-4H-benzo[1,4]oxazin-3-one hemi-ethanedisulphonate,
R-8-{2-[4-(6-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one hemi-ethanedisulphonate, and
R-8-{2-[4-(7-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one hemi-ethanedisulphonate,
optionally in the form of the tautomers or mixtures of the tautomers thereof.

2. A compound according to claim 1, wherein said compound is selected from the group consisting of:
R-8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one maleate,
R-8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one maleate,
R-8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one maleate,
R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one maleate,
R-8-{2-[1,1-dimethyl-3-(2-oxo-benzoxazol-3-yl)-propylamino]-1-hydroxy-ethyl}-6-hydroxy-4H-benzo[1,4]oxazin-3-one maleate,
R-8-{2-[1,1-dimethyl-3-(6-methyl-2-oxo-2,3-dihydro-benzimidazol-1-yl)-propylaminol]-1-hydroxy-ethyl}-6-hydroxy-4H-benzo[1,4]oxazin-3-one tartrate,
R-8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one tartrate,
R-8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one tartrate,
R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one tartrate,
R-8-{2-[1,1-dimethyl-3-(2-oxo-benzoxazol-3-yl)-propylamino]-1-hydroxy-ethyl}-6-hydroxy-4H-benzo[1,4]oxazin-3-one tartrate,
R-8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one hemi-ethanedisulphonate,
R-8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one hemi-ethanedisulphonate,
R-8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one hemi-ethanedisulphonate,
R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one hemi-ethanedisulphonate, and
R-8-{2-[1,1-dimethyl-3-(2-oxo-benzoxazol-3-yl)-propylamino]-1-hydroxy-ethyl}-6-hydroxy-4H-benzo[1,4]oxazin-3-one hemi-ethanedisulphonate,
optionally in the form of the tautomers or mixtures of the tautomers thereof.

3. A compound according to claim 2, wherein said compound is selected from the group consisting of:
- R-8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one maleate,
- R-8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one tartrate, and
- R-8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one hemi-ethanedisulphonate, optionally in the form of the tautomers or mixtures of the tautomers thereof.

4. A compound according to claim 2, wherein said compound is selected from the group consisting of:
- R-8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one maleate,
- R-8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one tartrate, and
- R-8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one hemi-ethanedisulphonate, optionally in the form of the tautomers or mixtures of the tautomers thereof.

5. A compound according to claim 2, wherein said compound is selected from the group consisting of:
- R-8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one maleate,
- R-8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one tartrate, and
- R-8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one hemi-ethanedisulphonate, optionally in the form of the tautomers or mixtures of the tautomers thereof.

6. A compound according to claim 2, wherein said compound is selected from the group consisting of:
- R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one maleate,
- R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one tartrate, and
- R-8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one hemi-ethanedisulphonate, optionally in the form of the tautomers or mixtures of the tautomers thereof.

7. A compound according to claim 2, wherein said compound is selected from the group consisting of:
- R-8-{2-[1,1-dimethyl-3-(2-oxo-benzoxazol-3-yl)-propylamino]-1-hydroxy-ethyl}-6-hydroxy-4H-benzo[1,4]oxazin-3-one maleate,
- R-8-{2-[1,1-dimethyl-3-(2-oxo-benzoxazol-3-yl)-propylamino]-1-hydroxy-ethyl}-6-hydroxy-4H-benzo[1,4]oxazin-3-one tartrate, and
- R-8-{2-[1,1-dimethyl-3-(2-oxo-benzoxazol-3-yl)-propylamino]-1-hydroxy-ethyl}-6-hydroxy-4H-benzo[1,4]oxazin-3-one hemi-ethanedisulphonate, optionally in the form of the tautomers or mixtures of the tautomers thereof.

* * * * *